United States Patent [19]
Kornecki et al.

[11] Patent Number: 5,665,701
[45] Date of Patent: Sep. 9, 1997

[54] PLATELET MEMBRANE GLYCOPROTEIN F11 AND POLYPEPTIDE FRAGMENTS THEREOF

[75] Inventors: Elizabeth H. Kornecki; Yigal H. Ehrlich, both of Staten Island, N.Y.

[73] Assignee: The Research Foundation of State University of New York, Albany, N.Y.

[21] Appl. No.: 342,449

[22] Filed: Nov. 17, 1994

[51] Int. Cl.⁶ .......................... A61K 38/16; C07K 14/705
[52] U.S. Cl. .................. 514/8; 530/395; 530/380
[58] Field of Search .................... 435/69.1, 69.3; 536/23.5; 530/380, 395; 514/8

[56] References Cited

PUBLICATIONS

Kornecki et al., "Activation of Human Platelets by a Stimulatory Monoclonal Antibody," J Biol Chem 265(17):10042–10048 (Jun. 15, 1990).

*Primary Examiner*—Stephen Walsh
*Assistant Examiner*—Christine Saoud
*Attorney, Agent, or Firm*—Nixon, Hargrave, Devans & Doyle

[57] ABSTRACT

The subject invention provides a platelet membrane glycoprotein, designated F11, which serves as a receptor for the monoclonal antibody M.Ab.F11. The purified platelet membrane glycoprotein has a deglycosylated molecular weight of about 29 kD. A partial sequence for the glycoprotein is also provided, as well as expression vectors and systems for producing the glycoprotein or fragments thereof.

15 Claims, 18 Drawing Sheets

PLATELET MEMBRANE GLYCOPROTEIN F11 AND POLYPEPTIDE FRAGMENTS THEREOF

This invention was made with support under National Institute of Health Grant HL 3291 and National Heart Lung and Blood Institute Grant HL 0241203. The U.S. Government has certain rights in this invention.

FIELD OF THE INVENTION

This invention is directed to a platelet membrane glycoprotein and polypeptide fragments thereof, and more particularly to a platelet membrane glycoprotein designated F11 that specifically binds monoclonal antibody F11, or a polypeptide fragment thereof. The invention also relates to DNA coding for the glycoprotein and polypeptide fragments, and vectors and methods for producing the glycoprotein and polypeptide fragments.

BACKGROUND OF THE INVENTION

Throughout this document various references are referred to by their author and year of publication. Full citations for these references can be found immediately preceding the sequence listing. The contents of each of these references is hereby incorporated by reference in order to more fully describe the state of the art to which the subject invention pertains.

The significant role of platelet activation in hemostasis is well-documented. Platelet activation is necessary for platelet aggregation and secretion, and is initiated by the binding of agohist to receptors at the platelet surface. Over the last ten years, several laboratories have developed monoclonal antibodies to platelet membrane glycoproteins. These platelet membrane glycoproteins can serve as agohist receptors on the platelet membrane. The antibodies to these glycoproteins have been of great value in studies designed to elucidate the structure and function of these glycoproteins.

Most of the success in raising monoclonal antibodies to platelet receptors was in studies on the integrin cohesion receptor IIb/IIIa (Coller et al., 1983; Kornecki et al., 1984) and the adhesion receptor Ib/IX (Coller et al., 1983; Handa et al., 1986). Functional antibodies that inhibit the action of these receptors provided a large body of new information and have led to direct conclusions about the functions of these glycoprotein receptors. Such inhibitory antibodies were also shown to have potential in vivo therapeutic use (Collet et al., 1986; Peters et al., 1986).

Some of these antibodies that serve as agonists, binding to the receptors at the platelet surface and thereby activating the platelets, have been identified. Several laboratories have developed or identified such "activator" antibodies that appear to react with platelet membrane protein components of 21–24 kD. The first report of a monoclonal antibody which served as an agonist and induced platelet aggregation was published by Boucheix et al. in 1983. This monoclonal antibody immunoprecipitated a platelet protein with apparent molecular weight (M.W.) of 24 kD under both reduced and non-reduced conditions. The addition of Fab fragments of this antibody to platelets resulted in the inhibition of platelet aggregation induced by various agonists. The platelet antigen recognized by this antibody was identical to the leukemia-associated antigen, p24, found in common acute lymphoblastic leukemia cells and neuroblastoma cells (Kersey et al., 1981; Jones et al., 1982; Komada et al., 1983). Thiagarajan et al. (1983) reported that platelet aggregation could be induced by another monoclonal antibody. This antibody was found to be directed against a 21 kD protein present in both normal and Glanzmann's thrombasthenic platelets.

Gorman et al. (1985) have described several monoclonal antibodies which induce platelet aggregation. All of these antibodies immunoprecipitated a 24 kD platelet protein in both the reduced and non-reduced states. The Fab fragments of these antibodies were found to augment the aggregation of platelets by adenosine diphosphate (ADP).

Higashihara et al. (1985) also described a monoclonal antibody which induced platelet aggregation and secretion by interaction with a protein of 24 kD. Preincubation of platelets with this antibody inhibited ristocetin-induced agglutination. It is known that these antibodies are directed against the p24/CD9 protein on the platelet surface. The CD9 antigen has been cloned and sequenced (Boucheix et al., 1991; Lanza et al., 1991), and CD9 antibodies have been shown to induce platelet aggregation mediated by the FcγRII receptor (CD32 molecule) (Worthington et al., 1990).

Duncan and Rosse (1986) showed that antibodies to platelet HLA class I antigen (anti-ABH IgG) could activate platelets and induce serotonin release. Similar results were obtained by Cosgrove et al. (1988), who reported that three different anti-HLA Class I monoclonal antibodies and an anti-$\beta_2$ microglobulin antibody caused platelet aggregation and secretion. Duncan and Rosse (1986) also showed that high concentrations of anti-Pl$^{A1}$ antibodies inhibited platelet secretion induced by these antibodies. Ryu et al. (1989) found that high concentrations of PL$^{A1}$ blocked fibrinogen binding resulting in the blockage of agohist-induced platelet aggregation, whereas low concentrations of anti-PL$^{A1}$ B antibodies induced release and aggregation.

Activator monoclonal antibodies directed against GPIIb and GPIIIa have also been reported. A stimulatory monoclonal antibody to the GPIIb/IIIa complex has been described by Modderman et al. (1988) which induces the release of alpha and dense granule contents resulting in platelet aggregation. Morel et al. (1989) have described a monoclonal antibody directed against GPIIb. The F(ab')$_2$ fragments of this antibody did not induce platelet aggregation although they blocked the stimulation of platelets by the intact antibody.

In addition to these antibodies, antibodies of other specificity have been described which activate platelets. Scott et al. (1989) described a monoclonal antibody which stimulates platelet secretion and aggregation and is directed against a platelet membrane glycoprotein of M.W. 67 kD. Recently, Yanabu et al. (1991) detected an autoantibody in a patient with immunothrombocytopenia (ITP), which activated normal platelets by interacting with a 36 kD platelet surface protein.

Kornecki et al. (1990) referred to a monoclonal antibody called M.Ab.F11 which induces vesicular secretion and aggregation in human platelets.

The health related significance of these antibodies which can activate human platelets is apparent. Characterization of the antigens which serve as receptors for these antibodies in the activation process is necessary as well as the elucidation of the biochemical pathways triggered by these interactions.

SUMMARY OF THE INVENTION

It is thus an object of the subject invention to provide an antigen which serves as a receptor in the platelet activation process. The particular antigen according to the subject invention is a platelet membrane glycoprotein, designated F11, which serves as a receptor for the monoclonal antibody, M.Ab.F11. Monoclonal antibody M.Ab.F11 has been deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, MD 20852 under ATCC Accession No. HB-11761 on Nov. 10, 1994. As indicated above, M.Ab.F11 induces platelet activation and has been referred to by Kornecki et al. (1990). The contents of this literature reference are hereby incorporated by reference in order to define the state of the art to which this invention pertains.

The purified platelet membrane glycoprotein, thus free of other substances of human origin, has a deglycosylated molecular weight of about 29 kD as determined by SDS-polyacrylamide gel electrophoresis. The amino acid sequence of this platelet membrane glycoprotein has been partially determined, and includes a first thirty-four (34) amino acids at the amino-terminal (N-terminal) having the sequence:

---
SEQ ID NO:1:
---

Xaa Val Thr Val His Ser Ser Glu Pro Glu Val Arg Ile
Pro Glu Asn Asn Pro Val Lys Leu Xaa Xaa Ala Tyr Xaa
Xaa Phe Gln Xaa Pro Xaa Ser Xaa.

Other portions of the amino acid sequence which have been determined include:

---
SEQ ID NO:2:
---

Xaa Xaa Xaa Xaa Xaa Thr Ile Tyr Leu Xaa Xaa Tyr;

SEQ ID NO:3:

Lys Phe Lys Leu Ile Val Leu Val;

SEQ ID NO:4:

Asp Xaa Xaa Xaa Xaa Xaa Xaa Xaa Ile Thr Phe Lys
Ser Val Thr Arg Xaa;

SEQ ID NO:5:

Xaa Xaa Xaa Xaa Xaa Xaa Xaa Xaa Xaa Xaa Xaa Xaa
Xaa Xaa Xaa Xaa Ile Xaa Xaa Xaa Xaa Xaa Xaa Xaa
Xaa Xaa Leu Xaa Xaa Xaa Xaa Xaa Lys Ser Val Thr
Arg Glu Asp Xaa Gly Xaa Xaa Leu Asp Met Xaa;

SEQ ID NO:6:

Xaa Thr Phe Leu Pro Thr Gly Ile Thr Phe Lys; and

SEQ ID NO:7:

Leu Xaa Asp Xaa Xaa Xaa.

Polypeptide fragments of the platelet membrane glycoprotein are provided by the subject invention, including non-naturally occurring polypeptides having an amino acid sequence substantially present in the monoclonal antibody M.Ab.F11 binding domain of platelet membrane glycoprotein F11.

The platelet membrane glycoprotein F11 and polypeptide fragments thereof according to the subject invention are capable of binding to M.Ab.F11, and can thus be used to inhibit platelet aggregation. This is accomplished because the glycoprotein and polypeptides bind to M.Ab.F11, thus preventing M.Ab.F11 from binding to the F11 receptor protein on the platelet surface. This in turn prevents activation of the platelets by M.Ab.F11, which prevents platelet aggregation which would otherwise be induced by M.Ab.F11.

Polypeptide fragments of the F11 platelet membrane glycoprotein include those with the following sequences: SEQ ID NO: 1, SEQ ID NO: 2, SEQ ID NO: 3, SEQ ID NO: 4, SEQ ID NO: 5, SEQ ID NO: 6, and SEQ ID NO: 7.

Having thus identified the F11 platelet membrane glycoprotein and polypeptide fragments thereof, expression systems can be devised for production of the glycoprotein and/or polypeptides using recombinant DNA technology. A plasmid is thus provided by the subject invention which includes DNA encoding the glycoprotein or polypeptide, and which further includes suitable regulatory elements positioned within the plasmid relative to the DNA encoding the glycoprotein or polypeptide so as to effect expression of the glycoprotein or polypeptide in a suitable host cell. A host cell, such as a bacterial cell, is genetically modified to include the plasmid DNA and regulatory elements, and when the host cell is cultured the glycoprotein or polypeptide is expressed and can be recovered. Purified DNA encoding the glycoprotein or polypeptide, which can be contained in the plasmid, is also included in the scope of the subject invention.

Since the glycoprotein and polypeptides according to the subject invention can be used to inhibit platelet aggregation, they may also be used to direct or target a compound such as a thrombolytic agent to platelets.

Each of these aspects of the subject invention is more fully discussed below.

BRIEF DESCRIPTION OF THE FIGURES

These and other objects, features and advantages of this invention will be evident from the following detailed description of preferred embodiments when read in conjunction with the accompanying drawings in which.

DETAILED DESCRIPTION OF THE INVENTION

Figure 1:
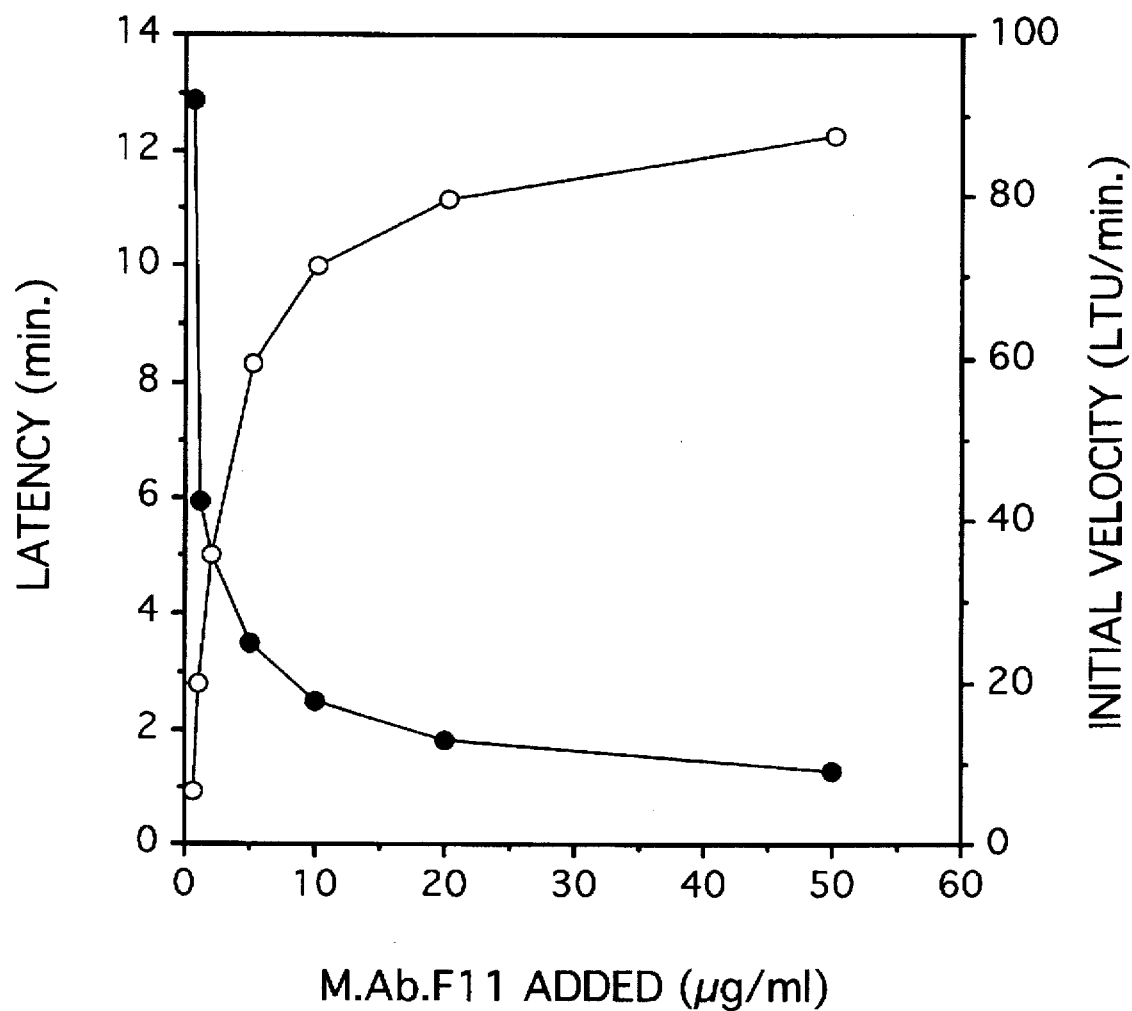
FIG. 1 shows the effect of increasing concentrations of M.Ab.F11 on the latency and initial velocity of platelet aggregation.

The invention provides a purified platelet membrane glycoprotein designated F11. This purified platelet membrane glycoprotein is free of other substances of human origin and has a deglycosylated molecular weight of about 29 kD as determined by SDS-polyacrylamide gel electrophoresis. F11 comprises one or more partial amino acid sequences selected from the group consisting of SEQ ID NO:1, SEQ ID NO:2, SEQ ID NO:3, SEQ ID NO:4, SEQ ID NO:5, SEQ ID NO:6, and SEQ ID NO:7. Fragments of this purified platelet membrane glycoprotein are also provided. The invention further provides non-naturally occurring polypeptides having an amino acid sequence substantially present in the monoclonal antibody M.Ab.F11 binding domain of platelet membrane glycoprotein F11. Examples of such non-naturally occurring polypeptides include polypeptides capable of inhibiting platelet aggregation having one or more of the following amino acid sequences:

---

SEQ ID NO:1:

Xaa Val Thr Val His Ser Ser Glu Pro Glu Val Arg Ile
Pro Glu Asn Asn Pro Val Lys Leu Xaa Xaa Ala Tyr Xaa
Xaa Phe Gln Xaa Pro Xaa Ser Xaa Xaa;

SEQ ID NO:2:

Xaa Xaa Xaa Xaa Xaa Thr Ile Tyr Leu Xaa Xaa Tyr;

SEQ ID NO:3:

Lys Phe Lys Leu Ile Val Leu Val;

SEQ ID NO:4:

Asp Xaa Xaa Xaa Xaa Xaa Xaa Xaa Xaa Ile Thr Phe Lys
Ser Val Thr Arg Xaa;

SEQ ID NO:5:

Xaa Xaa Xaa Xaa Xaa Xaa Xaa Xaa Xaa Xaa Xaa Xaa Xaa
Xaa Xaa Xaa Xaa Ile Xaa Xaa Xaa Xaa Xaa Xaa Xaa Xaa
Xaa Xaa Leu Xaa Xaa Xaa Xaa Xaa Xaa Lys Ser Val Thr
Arg Glu Asp Xaa Gly Xaa Xaa Leu Asp Met Xaa;

SEQ ID NO:6:

Xaa Thr Phe Leu Pro Thr Gly Ile Thr Phe Lys; and

SEQ ID NO:7:

Leu Xaa Asp Xaa Xaa Xaa.

---

The amino acid sequence as determined from the major peaks for each of these polypeptides is given below. As used herein, polypeptides may be, i.e., fragments of the purified platelet membrane glycoprotein F11; they may be produced using recombinant DNA techniques; or they may be synthesized in a peptide synthesizer. As would be understood by one skilled in the art, the term "having an amino acid sequence substantially present in the monoclonal antibody M.Ab.F11 binding domain of platelet membrane glycoprotein F11", as used herein, encompasses, i.e., naturally-occurring allelic variations and recombinant variations, such as site-directed mutagenesis. These are all encompassed by applicants' "polypeptide", the limitation being the ability to bind to monoclonal antibody M.Ab.F11.

As used herein, naturally-occurring platelet membrane glycoprotein F11 is as it occurs in the human body (on platelets). The polypeptides as disclosed herein have the biological activity of the M.Ab.F11 binding domain of naturally-occurring platelet membrane glycoprotein F11, which means that the polypeptides exhibit binding or adhesive properties similar to the M.Ab.F11 binding domain of naturally-occurring platelet membrane glycoprotein F11 when the level of such activity is assayed or determined.

The glycoprotein or polypeptide of the present invention is preferably produced in purified form by conventional techniques. Typically, the glycoprotein or polypeptide of the present invention is secreted into the growth medium of recombinant E. coli. To isolate the glycoprotein or polypeptide, the E. coli host cell carrying a recombinant plasmid is propagated, homogenized, and the homogenate is centrifuged to remove bacterial debris. The supernatant is then subjected to sequential ammonium sulfate precipitation. The fraction containing the glycoprotein or polypeptide of the present invention is subjected to gel filtration in an appropriately sized dextran or polyacrylamide column to separate the proteins or polypeptides. If necessary, the protein or polypeptide fraction may be further purified by HPLC.

The DNA molecule encoding platelet membrane glycoprotein F11 or polypeptide fragments thereof can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted glycoprotein or polypeptide coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following vital vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif, which is hereby incorporated by reference), pQE, pIH821, pGEX, pET series (see F. W. Studier et. al. (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al. (1982), which is hereby incorporated by reference.

A variety of host-vector systems may be utilized to express the glycoprotein- or polypeptide-encoding sequence (s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promotors and accompanying genetic signals may not be recognized in or may not function in a procaryotic system, and, further, procaryotic promotors may not be recognized and may not function in eucaryotic cells.

Similarly, translation of mRNA in procaryotes depends upon the presence of the proper procaryotic signals which differ from those of eucaryotes. Efficient translation of mRNA in procaryotes requires a ribosomal binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16 S rRNA (ribosomal RNA) and probably promote binding of mRNA to ribosomes by duplexing with the rRNA to allow correct positioning of the ribosome. For a review on maximizing gene expression, see Roberts and Lauer (1979), which is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in $E.$ $coli$, its bacteriophages, or plasmids, promotors such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other $E.$ $coli$ promotors produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-β-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in $E.$ $coli$ requires a Shine-Dalgarno (SD) sequence about 7–9 bases 5' to the initiation codon (ATG) to provide a ribosomal binding site. Thus, any SD-ATG combination that can be utilized by host cell ribosomes may be employed. Such combinations include but are not limited to the SD-ATG combination from the cro gene or the N gene of coliphage lambda, or from the $E.$ $coli$ tryptophan E, D, C, B or A genes. Additionally, any SD-ATG combination produced by recombinant DNA or other techniques involving incorporation of synthetic nucleotides may be used.

Once the isolated DNA molecule encoding the platelet membrane glycoprotein or polypeptide fragment thereof has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, and the like.

The subject invention also provides a platelet membrane glycoprotein or polypeptide as disclosed above bound to a thrombolytic agent. The thrombolytic agents may be selected from, for example, tissue plasminogen activator (TPA), urokinase, streptokinase, prourokinase, anisoylated plasminogen-streptokinase activator complex, TPA analogs, or a protease. As used throughout the subject application, "bound" encompasses being bound covalently, non-covalently, or conjugated. The glycoprotein or polypeptides may be conjugated through other chemical moieties including amino acid or polypeptide cross-linkers, which are standardly used in the art and are well-known to those skilled in the art to which the subject invention pertains.

The details of the subject invention are disclosed more fully below in the context of experiments. The first set of data provides direct evidence that the stimulatory antibody (M.Ab.F11) activates platelets by crosslinking the F11 receptor with the FcγRII receptor through formation of intraplatelet bridges (Example 1). The second set of data provides evidence for the purification and characterization of the human platelet membrane glycoprotein F11 (Example 2).

EXAMPLE 1

Experimental Procedures

Materials: Trizma base, Me$_2$SO, sodium chloride, EGTA, potassium chloride, BSA, sodium dihydrogen phosphate, Hepes, SDS, sucrose, glucose, PGEm, and apyrase grade V were purchased from Sigma Chemical Co. (St. Louis, MO). Polyacrylamide, Coomassie-brilliant blue R-250, molecular weight markers, and bis-acrylamide were obtained from BioRad (Melville, NY). Immobilized papain, Iodo beads, protein A agarose, immunopure binding buffer and immunopure elution buffer were purchased from Pierce (Rockford, IL). $^{125}$I-Iodine and $^{32}$P-phosphate were obtained from Amersham (Arlington Heights, IL). Luciferin-luciferase reagent was purchased from Chronolog Corp. (Haverstown, PA). Aequorin was obtained from Friday Harbor Photoproteins (Friday Harbor, WA). α-Thrombin was obtained from the New York State Department of Health (Albany, NY). All other reagents used were analytical grade.

Monoclonal antibodies: M.Ab.F11 (IgG$_1$) and Fab fragments were produced and purified as previously described (Kornecki et al., 1990). Monoclonal antibody M.Ab.F11 is available from the American Type Culture Collection as ATCC Accession No. HB-11761. CD32 antibody IV.3 (IgG$_{2b}$) was purchased from Mederax, Inc. (West Lebanon, NH). A panel of 110 monoctonal antibodies was obtained from Cornell University Medical Center (New York, NY).

Blood Collection and Platelet Preparation: Blood collection and platelet isolation were carried out as described by Kornecki et al. (1990). Blood was obtained from individuals who were free of any medication for at least 2 weeks prior to experimentation. Venous blood was collected into acid citrate dextrose (ACD, 6:1). Platelet-rich plasma was prepared by centrifugation at 200×g for 10 minutes at 24° C. Platelets were washed three times using Tyrode's-BSA (0.35%) solution buffered with 20 mM Hepes, 2 mM calcium chloride, 11.9 mM sodium bicarbonate, 0.36 mM sodium dihydrogen phosphate, 5.5 mM glucose, and 1 mM magnesium chloride, following the procedure of Mustard et al. (1972). The first wash contained 1 µM PGE$_1$, 1 unit/ml apyrase, and 2 unit/ml of heparin; the second wash lacked heparin; and the third wash contained only Pge$_1$. The platelet pellet was re-suspended in Tyrode's-BSA buffer (without inhibitors) and counted on a hemocytometer using a phase contrast microscope.

Platelet Aggregation: The platelet aggregation experiments were carried out in a Chronolog lumi-aggregometer (Chronolog Corp., Haverstown, PA). Platelet suspensions (0.45 ml) containing 2–4×10$^8$ platelets per ml were placed in a siliconized cuvette and aggregation was initiated by the addition of M.Ab.F11 (10 µg) with constant stirring at 1200 rpm at 37° C. Platelet secretion, measured as release of adenosine triphosphate (ATP), was monitored by adding 50 µl of luciferin/luciferase reagent.

Iodination of Antibodies and Antibody Binding to Platelets: Purified monoclonal antibodies and Fab fragments were radiolabeled using Iodo-Beads (Walkowiak et al., 1992). Binding of radiolabeled antibodies to platelet-rich plasma or to washed platelets (2–4×10$^8$ platelets/ml) was performed over a 200 µl cushion of 20% sucrose. The incubation mixture consisted of 90 µl of a platelet suspension (2–4×10$^8$ platelets/ml) and radiolabeled monoclonal antibodies in a total volume of 100 µl.

Preparation of the Fragments of M.Ab.F11: M.Ab.F11 IgG was enzymatically digested for 20 hours at 37° C. using the immobilized papain for the generation of Fab and Fc fragments. The F(ab')$_2$ fragments were generated by digesting with immobilized ficin following the procedure detailed by the Pierce Chemical Company (Rockford, IL). The fragments were separated from each other by protein A column chromatography.

Intracellular Calcium: Intracellular free calcium levels were measured following the procedure of Yamaguchi et al. (1986) using aequorin-loaded platelets in a PICA-Lumi aggregometer (Chronolog Corp., Haverstown, PA). Washed platelet suspensions (10$^{10}$/ml) were incubated at 24° C. for 2 minutes with 1 mg/ml of aequorin and Me$_2$SO was added in six increments to obtain a final concentration of 6%. The incubation was continued for two minutes before diluting with 0.9 ml of suspension buffer containing 1 mM EDTA. The platelets were collected with a brief spin of one minute in an eppendorf microfuge and re-suspended (2–5×10$^8$ platelet/ml) in Tyrode's-BSA buffer. Aliquots (0.98 ml) were placed in a PICA-aggregometer at 37° C. and aggregation and intracellular calcium levels were recorded using a dual channel recorder.

$^{14}$C-Serotonin Release: [$^{14}$C]5-Hydroxy tryptamine creatinine sulfate (serotonin, 58 mCi/mMol) was added to platelet-rich plasma and incubated for thirty minutes at 24° C. as previously described (Kornecki and Feinberg, 1980). Imipramine (2 µM) was added to prevent re-incorporation and incubation continued for five minutes. Formaldehyde (135 mM) was added to stop the release reaction and platelet suspensions were centrifuged for one minute at 12,000×g. [$^{14}$C]-serotonin release was measured by counting 50 µl of the supernatant in a scintillation counter.

Protein Phosphorylation in Platelets Labeled with $^{32}$P: Platelets were labeled with $^{32}$P-phosphorous as described previously (Naik et al., 1991). Washed platelets (10$^9$/ml), resuspended in phosphate-free Tyrode's buffer containing BSA (pH 7.4), were incubated with 1 mCi/ml of $^{32}$P for sixty minutes at 37° C. The platelets were washed and re-suspended in phosphate-containing, BSA-free Tyrode's solution. Aliquots (50 µl) of the platelet suspension were incubated with agonists at 37° C. under non-stirring conditions. The reactions were stopped by the addition of 50 µl of SDS-Laemmli solution containing 5% β-mercaptoethanol (final concentration) and processed for SDS-PAGE followed by autoradiography. Radiolabeled $^{32}$P-phosphate incorporation into the phosphoproteins was quantitated by excising the 40 kD and 20 kD protein bands from the dried gels and counting the radioactivity using a scintillation counter.

SDS-PAGE: SDS-PAGE was performed in 3% stacking gels and in 5–15% gradient separation polyacrylamide slab gels according to the procedure of Laemmli (1970). The gels were stained for proteins with Coomassie Brilliant Blue, de-stained in 10% acetic acid, 20% methanol, dried in vacuo, and exposed to Kodak X-Omat AR film with Dupont-Cronex Lightning Plus intensifying screens for approximately 1–2 hours at −70° C. and developed in a Kodak X-Omat developer (Eastman Kodak Company, Rochester NY). Molecular weight determinations were made by comparison with standard molecular weight markers (BioRad, Melville, NY).

F11 Receptor Protein Purification: The F11 receptor protein corresponding to the 32 kD band was purified from outdated platelet concentrates. In brief, the platelet concentrates were washed three times and re-suspended in 20 mM Tris-HCl buffer, pH 8.0, containing phenyl methyl sulfonyl fluoride (PMSF) (2 mM), leupeptin (10 µg/ml), aprotinin (10 µg/ml), iodoacetamide (20 mM), benzamidine-HCl (5 mM) and soybean trypsin inhibitor (10 µg/ml). The platelets were lysed using a nitrogen bomb and the platelet membrane fractions were collected following ultracentrifugation (100,000×g for 1 hour at 4° C.). The membrane proteins were extracted using 1% nonidate P-40. F11 receptor protein was purified using DEAE Sepharose Fast Flow column chromatography followed by M.Ab.F11 (5mg/ml of gel) affinity chromatography.

Platelet Activation by M.Ab.F11: The induction of platelet aggregation and secretion by M.Ab.F11 was found to be dependent on M.Ab.F11 concentration in two ways. FIG. 1 illustrates the effect of increasing concentrations of M.Ab.F11 on the latency and initial velocity of platelet aggregation. Platelet suspensions (0.45 ml) were incubated with various concentrations of M.Ab.F11. The aggregation response was monitored using a lumiaggregometer. The darkened circle represents latency, i.e., the time elapsed from the addition of M.Ab.F11 to the onset of aggregation. The open circle represents the initial velocity of aggregation. As shown, an increase in the M.Ab.F11 concentration resulted in a shortened latency and in an enhanced initial velocity of platelet aggregation. In the experiment shown in FIG. 1, maximal aggregation was achieved at a concentration of 20 µg/ml.

Figure 2:
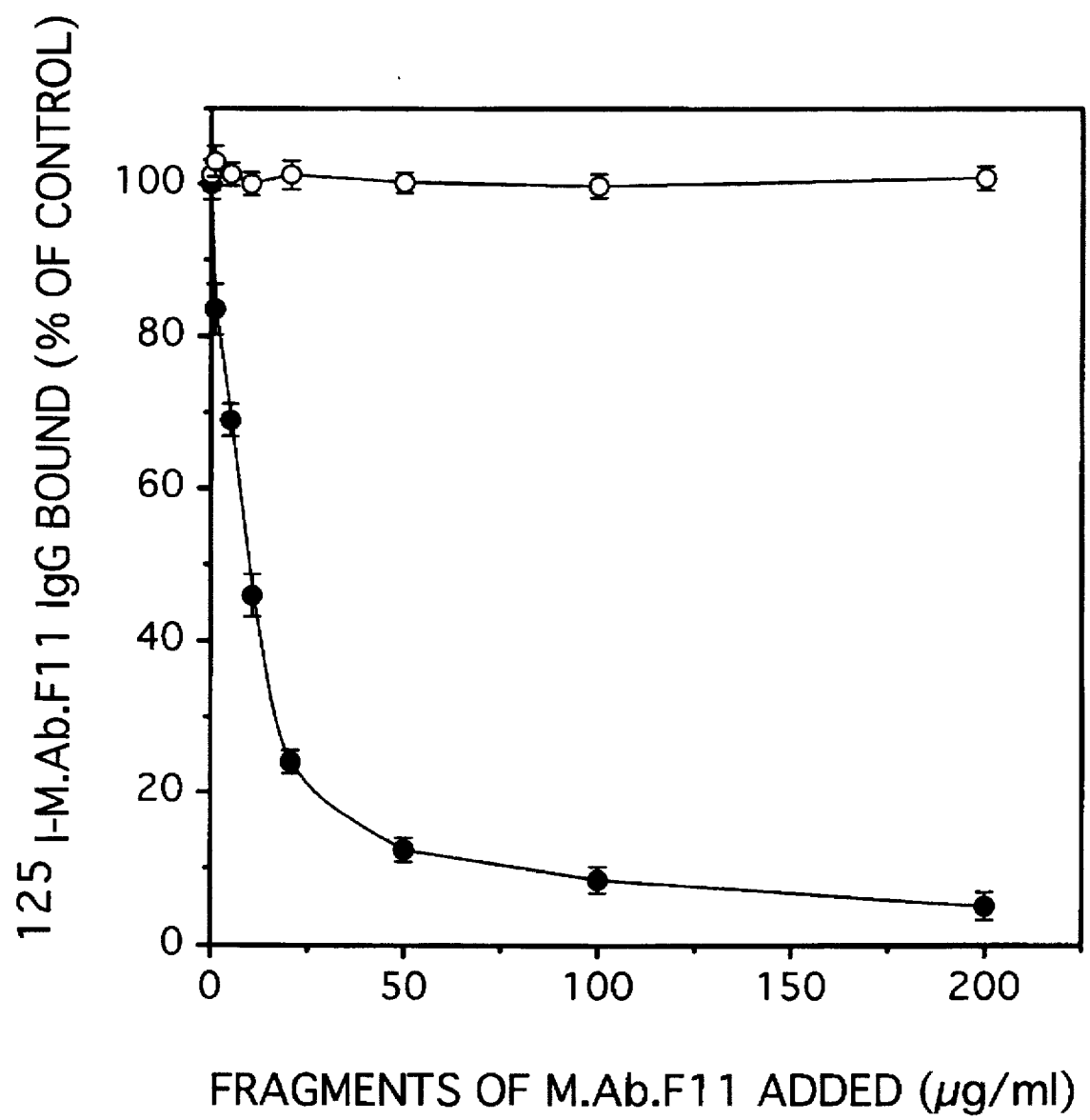
FIG. 2 shows the inhibition of binding of $^{125}$I-M.Ab.F11 to human platelets by Fab fragments of M.Ab.F11.

Both Fab and Fc fragments of M.Ab.F11, generated by papain proteolytic digestion, failed to stimulate platelets. However, only Fab fragments inhibited M.Ab.F11-induced platelet aggregation. FIG. 2 illustrates this inhibition of the binding of $^{125}$I-M.Ab.F11 to human platelets by Fab fragments of M.Ab.F11. Platelet suspensions were incubated simultaneously with varying concentrations of Fab or Fc fragments of M.Ab.F11 and with a constant amount of $^{125}$I-labeled M.Ab.F11 IgG at 37° C. for 15 minutes. Specific binding of $^{125}$I-M.Ab.F11 was determined as described in the Experimental Procedures. As shown in FIG. 2, Fab fragments (represented by the darkened circle) completely inhibited the specific binding of $^{125}$I-labeled M.Ab.F11 IgG; Fc fragments alone (represented by the open circle), up to a concentration of 200 µg/ml, did not inhibit the binding nor the aggregation. The concentration of Fab which produced half-maximal inhibition was approximately 9.5 µg/ml, and complete inhibition occurred between 50–100 µg/ml. In addition, F(ab')2 fragments (11 µg/ml) completely blocked M.Ab.F11-induced platelet aggregation similar to that observed with Fab fragments.

Figure 3:
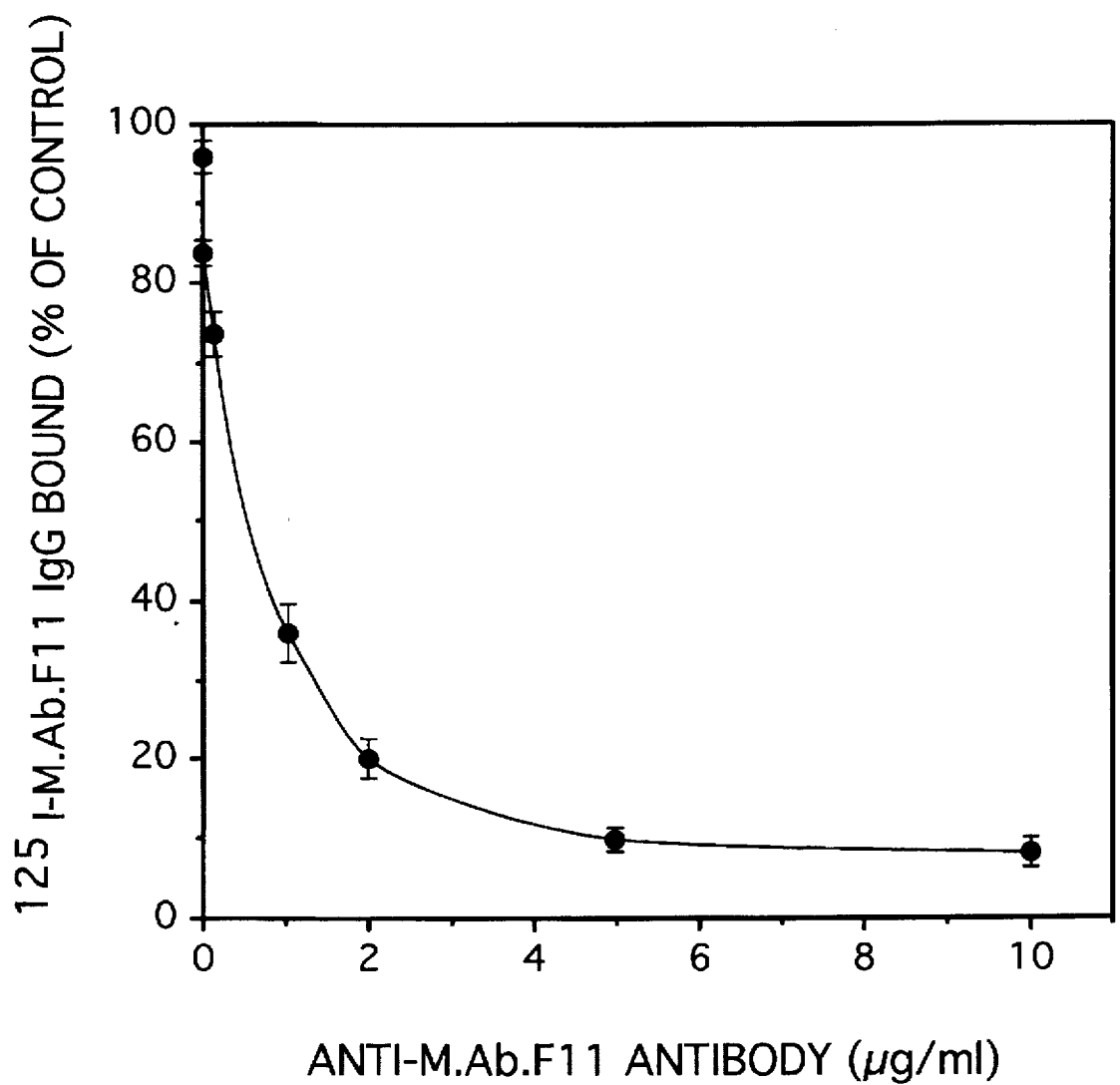
FIG. 3 shows the inhibition of binding of $^{125}$I-M.Ab.F11 to platelets by anti-M.Ab.F11 antibodies.

Polyclonal antibodies developed against M.Ab.F11 also completely abolished the binding of $^{125}$I-M.Ab.F11 to platelets. FIG. 3 illustrates this inhibition of binding of $^{125}$I-M.Ab.F11 to platelets by anti-M.Ab.F11 antibodies. Specific binding of $^{125}$I-labeled M.Ab.F11 to platelets in the presence of varying concentrations of anti-M.Ab.F11 polyclonal antibodies (antiserum) was done as described in the Experimental Procedures. As shown, half-maximal inhibition by these polyclonal antibodies occurred at a concentration of 0.6 µg/ml and complete inhibition occurred at 5 µg/ml antibody.

Figure 4:
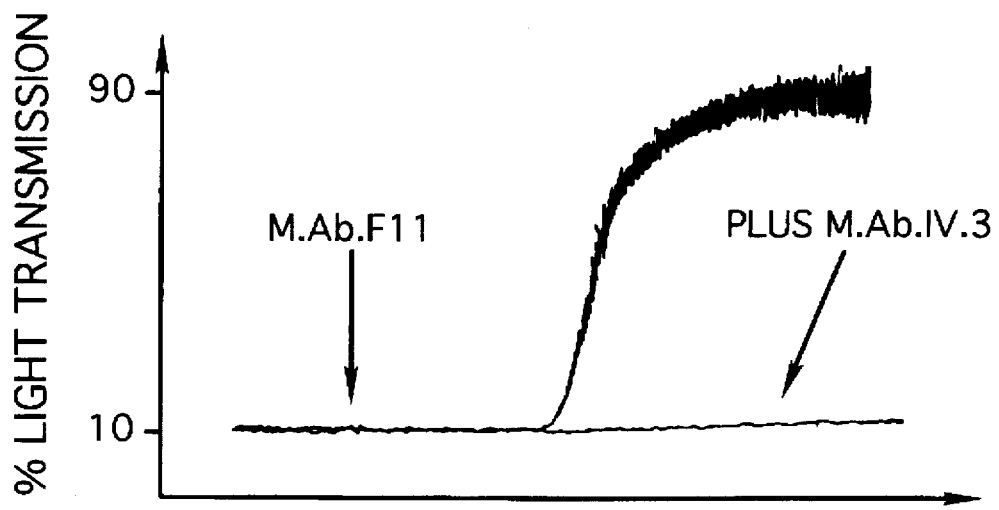
FIGS. 4 and 5 show the inhibition of platelet aggregation and secretion induced by M.Ab.F11 by anti-FcγRII antibody (M.Ab.IV.3)
Figure 5:
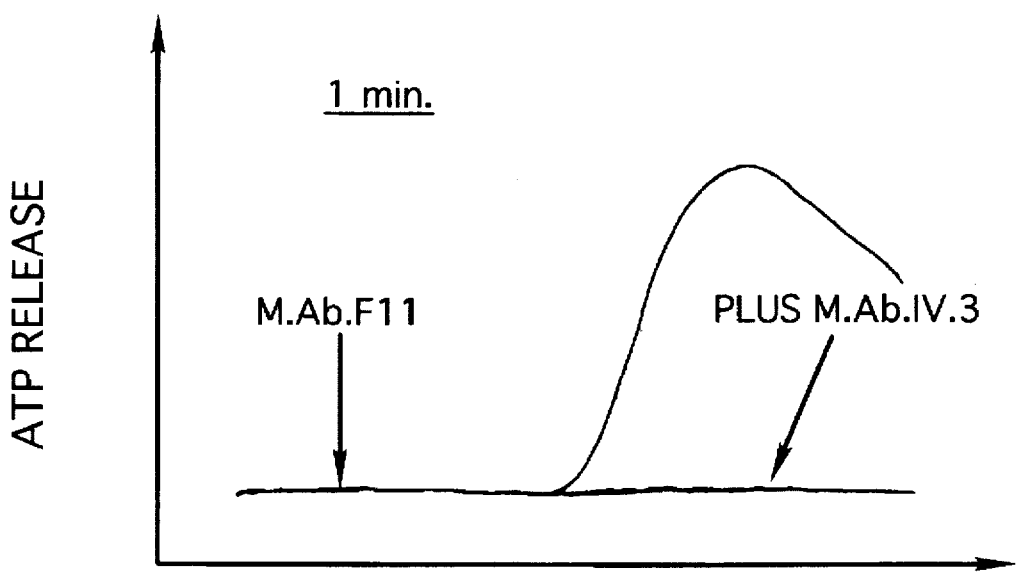

Inhibition of M.Ab.F11 Induced Platelet Aggregation and Secretion by Antibody to the Fc Receptor Epitope: FIGS. 4 and 5 show the effect of anti-FcγRII antibody (M.Ab.IV.3) on M.Ab.F11-induced platelet aggregation and granular secretion. Aliquots (0.45 ml) of washed platelets were incubated for 1–2 minutes at 37° C. with 50 µl of a luciferin/luciferase reagent solution in a Chronolog Lumi-Aggregometer. Aggregation (FIG. 4) and secretion of ATP (FIG. 5) were initiated by the addition of M.Ab.F11 (10 µg/ml). M.Ab.IV.3 (10 µg/ml) was added 2 minutes prior to addition of M.Ab.F11. In the presence of M.Ab.IV.3, the M.Ab.F11-induced platelet aggregation (FIG. 4) and ATP secretion (FIG. 5) were completely blocked.

Figure 6:
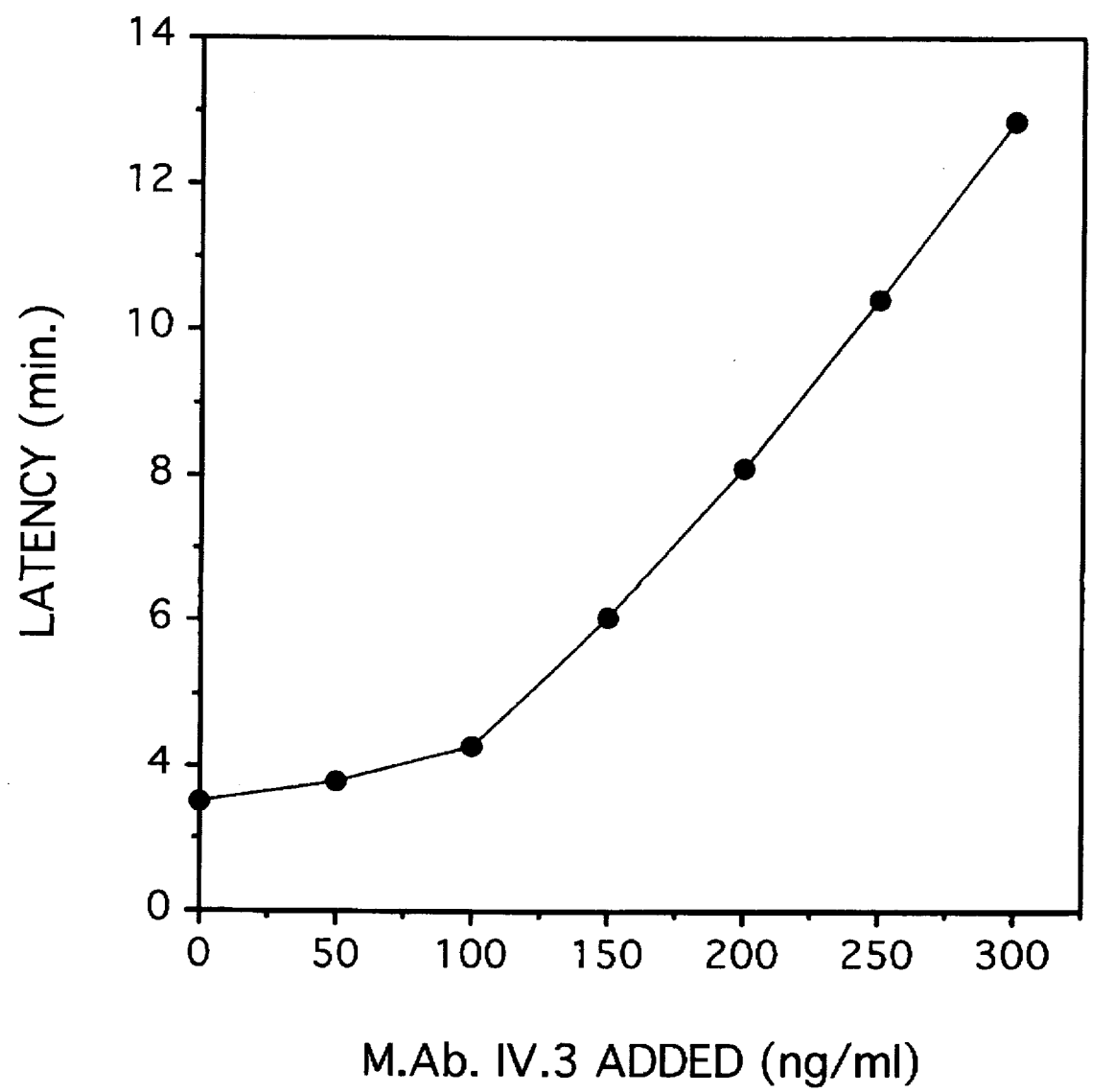
FIG. 6 is a dose response curve showing the effect of anti-Fc receptor antibody (M.Ab.IV.3) on M.Ab.F11-induced platelet aggregation.

FIG. 6 is a dose-response curve showing the effect of anti-Fc receptor antibody (M.Ab.IV.3) on M.Ab.F11-induced platelet aggregation. Washed platelets were incubated with increasing concentrations of M.Ab.IV.3 in a lumiaggregometer for 2 minutes prior to addition of 10 µg/ml M.Ab.F11. Latency is the time interval (minutes) elapsed from the addition of M.Ab.F11 to the onset of platelet aggregation. FIG. 6 shows that the addition of IV.3 increased the latency of M.Ab.F11-induced aggregation in a dose-dependent manner. A concentration of approximately 150 ng/ml doubled the time for induction of aggregation by M.Ab.F11. The addition of a concentration of 500 ng/ml of M.Ab.IV.3 resulted in a complete blockage of M.Ab.F11-induced platelet aggregation (even after a 12 hour period following the addition of M.Ab.F11).

Figure 7:
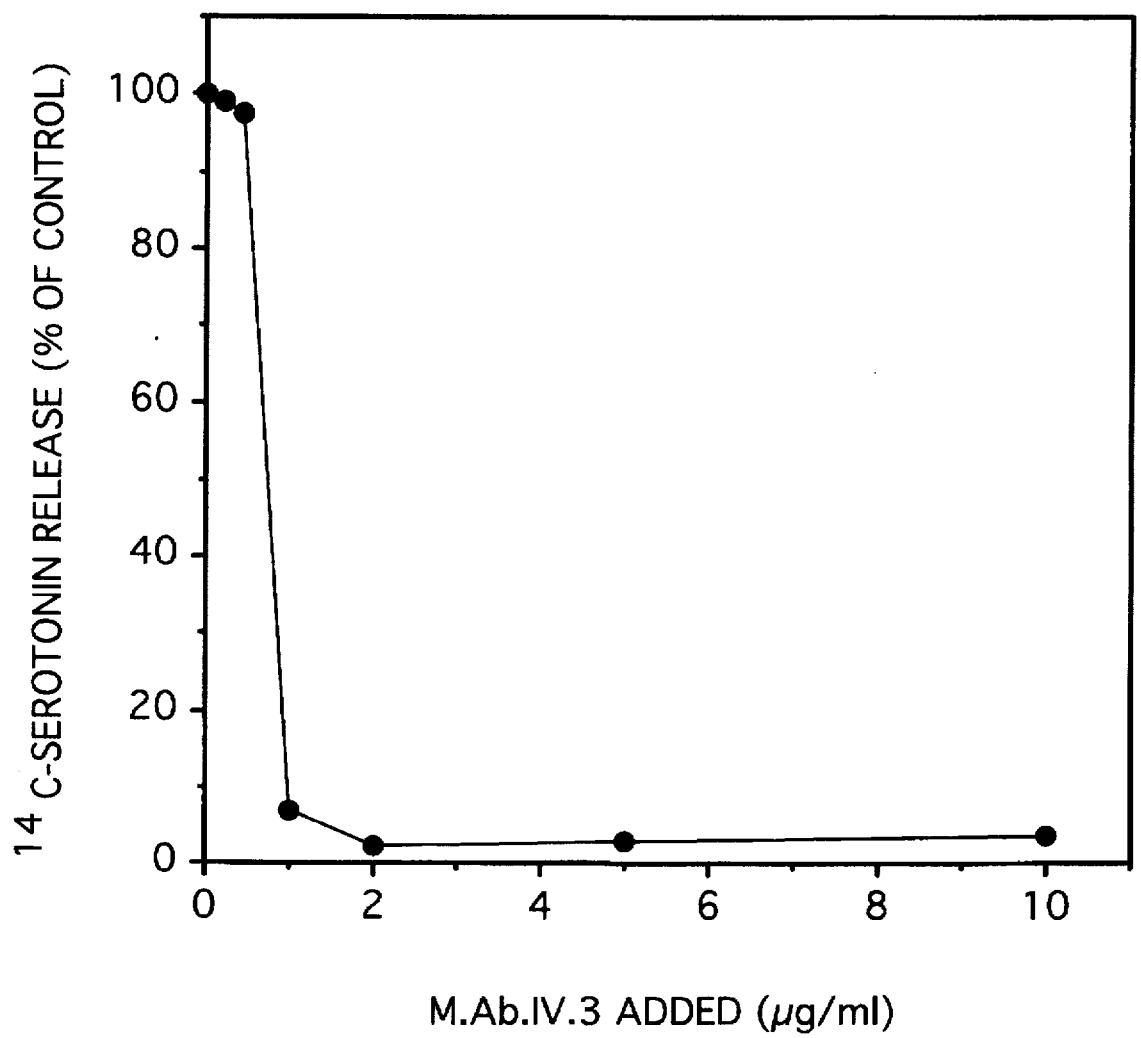
FIG. 7 shows the inhibition of M.Ab.F11-induced $^{14}$C-serotonin release by M.Ab.IV.3.

FIG. 7 illustrates the inhibition of M.Ab.F11-induced $^{14}$C-serotonin release by M.Ab.IV.3. Platelets were loaded with $^{14}$C-serotonin as described in the Experimental Procedures. Aliquots (0.45 ml) were incubated for 2 minutes at 37° C. with various concentrations of M.Ab.IV.3 in an aggregometer. M.Ab.F11 (5 µg/ml) was added to initiate platelet aggregation. Incubations were continued for 7 minutes after which 50 µl aliquots were processed for $^{14}$C-serotonin release. As shown, the release of $^{14}$C-serotonin induced by M.Ab.F11 was inhibited by M.Ab.IV.3 in an all-or-none manner. At low concentrations (less than 200 ng/ml), M.Ab.IV.3 did not inhibit m$^{14}$C-serotonin release, whereas, at concentrations of approximately 1 µg/ml, IV.3 completely blocked the release of serotonin when platelets were stimulated by M.Ab.F11.

Figure 8:
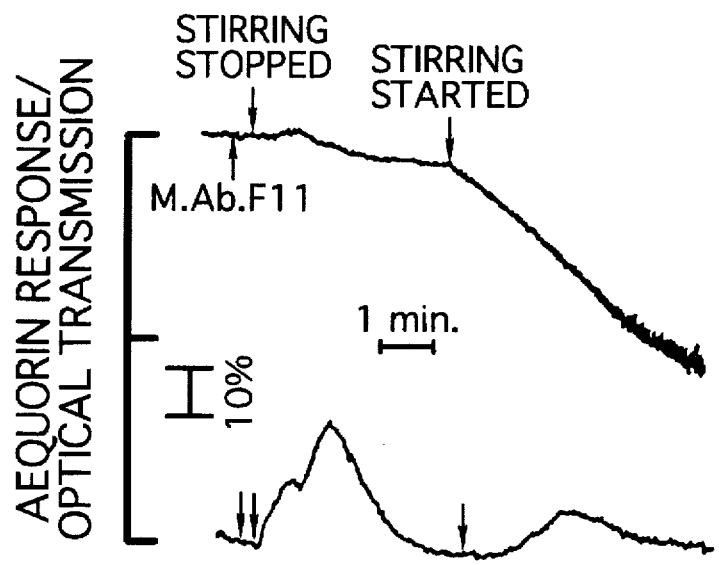
FIGS. 8 and 9 show the inhibition of the effect of M.Ab.F11 on intracellular $Ca^{++}$ levels by M.Ab.IV.3.
Figure 9:
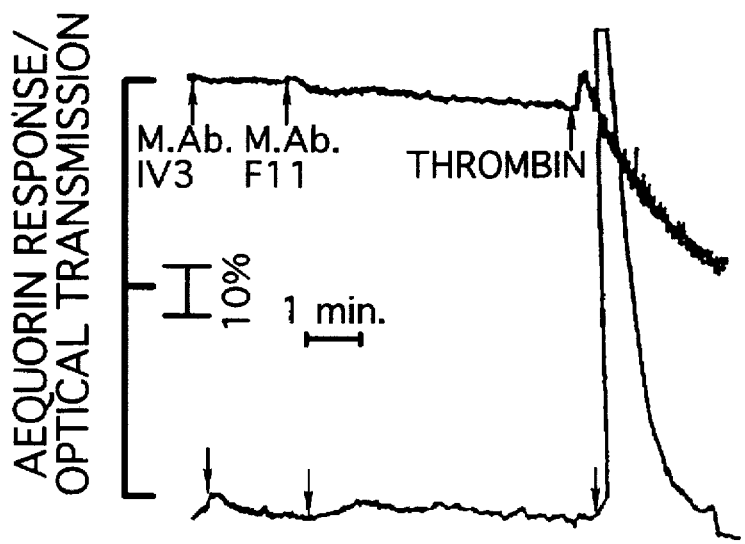

Effect of M.Ab.IV.3 on Intracellular Calcium Transients Induced by M.Ab.F11: FIGS. 8 and 9 show the inhibition (by M.Ab.IV.3) of the effects of M.Ab.F11 on intracellular $Ca^{++}$ levels. Platelets were incubated with the photoprotein aequorin following the procedure of Yamaguchi et al. (1986) and Kornecki and Ehrlich (1988). In FIG. 8, aequorin-loaded platelet suspensions (2–3×10$^8$ platelets/ml) were stimulated with M.Ab.F11 (see 1st arrow). The upper tracing indicates aggregation; the lower tracing represents the $Ca^{++}$ response. Fifteen (15) seconds after addition of M.Ab.F11, stirring was stopped for 4 minutes (between the 2nd and 3rd arrow) and then re-started to initiate aggregation. In FIG. 9, M.Ab.IV.3 (1 µg/ml) was added (indicated by 1st arrow) 2 minutes prior to the addition of M.Ab.F11 (as shown by 2nd arrow) with continued stirring. Thrombin (0.2 unit/ml) was added 5 minutes later to determine whether aggregation and a $Ca^{++}$ response could be elicited under these conditions. Following the addition of M.Ab.F11 to the aequorin-loaded platelet suspensions, a primary calcium signal, indicating M.Ab.F11-induced increase in intracellular free $Ca^{++}$ levels, was observed within thirty seconds under non-stirring conditions (FIG. 8). This primary signal was followed by a smaller secondary calcium signal which paralleled platelet aggregation (initiated by stirring, FIG. 8). Both calcium signals were blocked by the presence of 5 mM EGTA indicating a role of extracellular calcium in these events. Preincubation of platelets with M.Ab.IV.3 (1 µg/ml) also resulted in inhibition of both the calcium signal and aggregation in response to M.Ab.F11 (FIG. 9). In contrast, M.Ab.IV.3 (1 µg/ml) did not inhibit the aggregation nor the calcium signal induced by thrombin (1 unit/ml) indicating the involvement of separate pathways in platelet activation dependent on the agohist.

Figure 10:
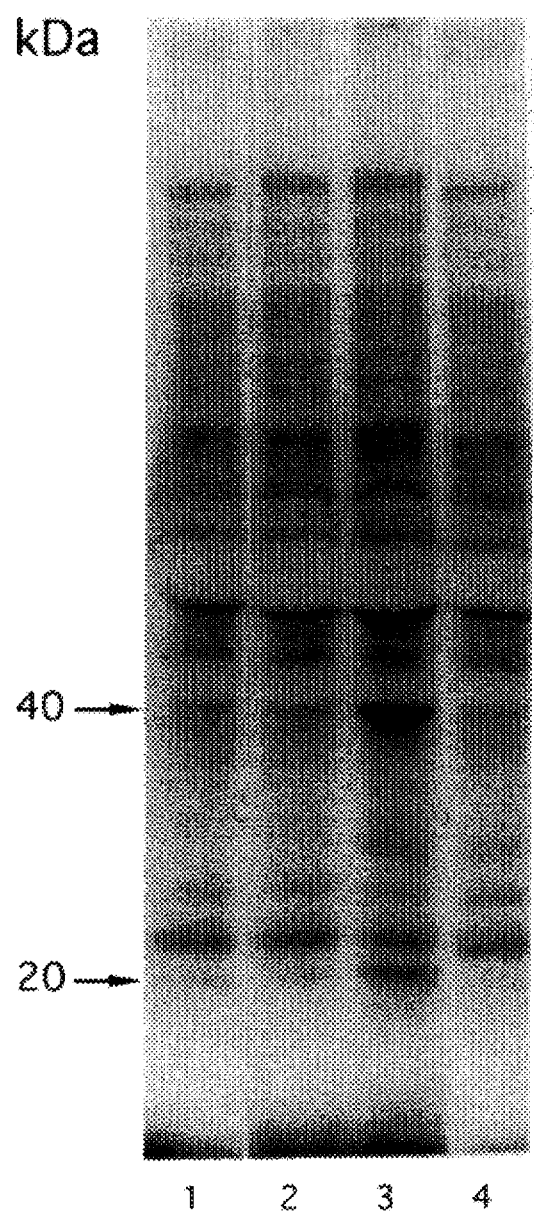
FIGS. 10 and 11 show the effect of M.Ab.IV.3 on the enhanced phosphorylation of 40 kD and 20 kD proteins induced by M.Ab.F11.
Figure 11:
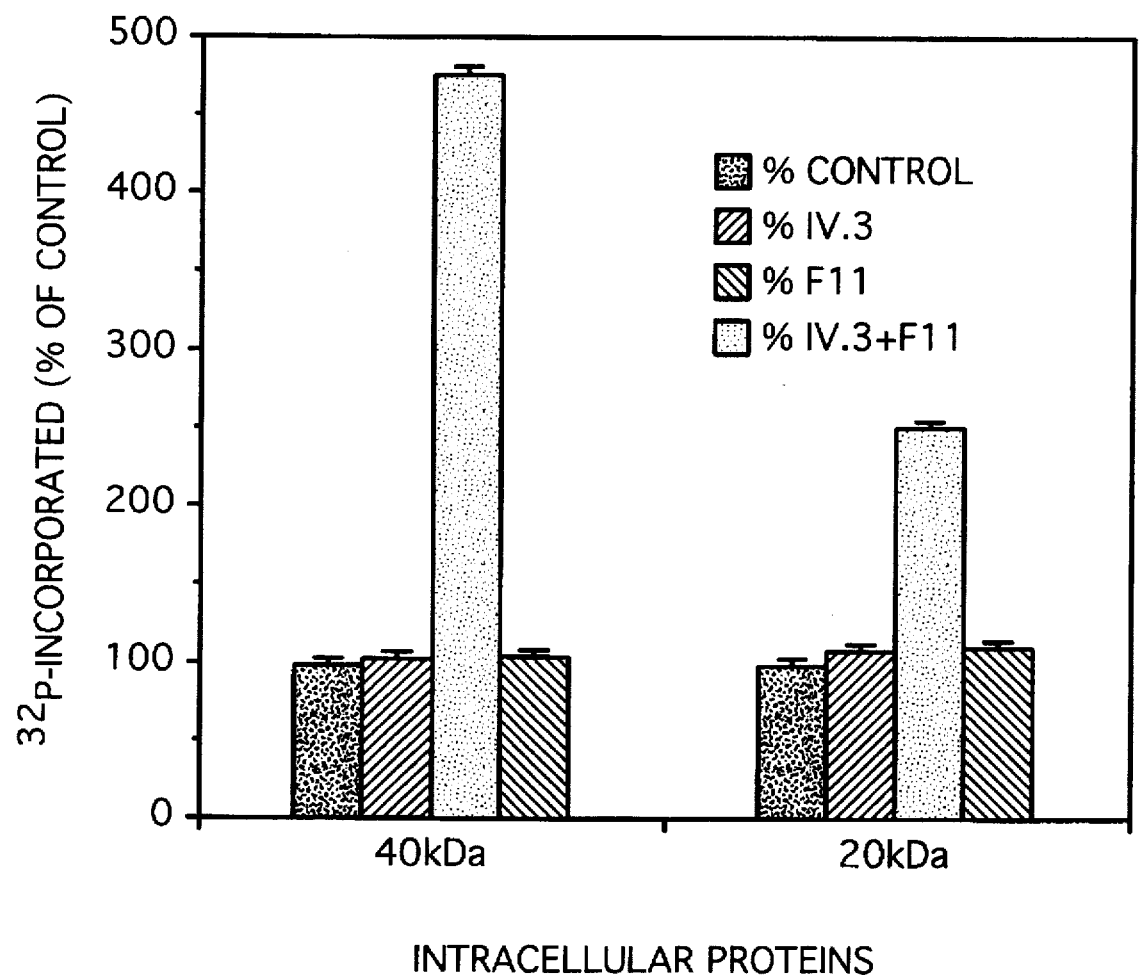

Inhibition of M.Ab.F11 Stimulated Intracellular Phosphorylation of 40 kD and 20 kD proteins by M.Ab.IV.3: The effect of M.Ab.IV.3 on the M.Ab.F11-induced phosphorytation of 40 kD (p47) and 20 kD (p20) intracellular proteins is shown in FIGS. 10 and 11. $^{32}$P-labeled washed platelets were incubated with M.Ab.IV.3 for 5 minutes at 37° C. prior to the addition of M.Ab.F11 (10 µg/ml). The platelet proteins were then extracted in SDS-buffer and analyzed by SDS-PAGE followed by autoradiography. The bands corresponding to the 40kD and the 20kD proteins were cut and the amount of the $^{32}$P-incorporated was determined by scintillation counting. FIG. 10 shows the autoradiograph (Lane 1, control; Lane 2, M.Ab.IV.3 alone; Lane 3, M.Ab.F11 alone; and Lane 4, preincubation of platelets with M.Ab.IV.3 followed by the addition of M.Ab.F11). FIG. 11 shows the $^{32}$P incorporated into the 40 kD and 20 kD proteins under the identical conditions described in FIG. 10. As shown, M.Ab.F11 induced a selective increase in the phosphorylation of the 40 kD (p47) and 20 kD (p20) proteins (FIG. 10, lane 3). Quantitation of p47 and p20 indicates that there is a 5-fold and 2.5-fold increase, respectively, in the phosphorylation of these proteins (FIG. 11). The enhanced phosphorylation of both proteins was completely inhibited by M.Ab.IV.3 (FIG. 10, lane 4 and FIG. 11). M.Ab.IV.3 alone had no effect on the phosphorylation of these proteins (FIG. 10, lane 2), compared to basal (control) levels (also see FIG. 10). These results indicate that the intracellular signals induced by M.Ab.F11 are dependent on the action of the FcγRII receptor.

Lack of Effect of CD9 Monoclonal Antibodies and Various Other Antibodies on M.Ab.F11 binding to human platelets: Since several monoclonal antibodies specific to the CD9 antigen are known to induce platelet activation, their potential interaction with the F11 receptor was investigated. Various monoclonal antibodies specific to the CD9 antigen were added to platelet suspensions prior to the addition of the $^{125}$I-labeled M.Ab.F11 and the specific binding of M.Ab.F11 was determined. As shown in Table 1, CD9 monoclonal antibodies had no effect (neither stimulatory nor inhibitory) on the binding of M.Ab.F11 to its receptor; only unlabeled (cold) M.Ab.F11 resulted in the displacement (97%) of $^{125}$I-M.Ab.F11. These results indicate that the F11 receptor is distinct from the platelet CD9 antigen. A similar lack of inhibition of $^{125}$I-M.Ab.F11 binding was observed with antibodies directed against CD31, CD32, CD36, CD41, CD42, CD42a, CD42b, CD61, CD62, CD63, LAMP 1 and LAMP 2, as well as with the following monoclonal antibodies: 14A2.M1, 105.12C9A3, 105.12E2.H5, WDS10.D8, GRV1, D6A7/A1, P4-7, T-28, Ruu SP1.77, IB3, GI11, GI34, GI21, 7D1, 8A3, SW16, P3-38, NAM81-1B2, D5-45, and AMF7 (all obtained from the Fifth International Workshop in Leukocyte Differentiation Antigens). These results further indicate the uniqueness of the platelet F11 receptor.

Figure 12:
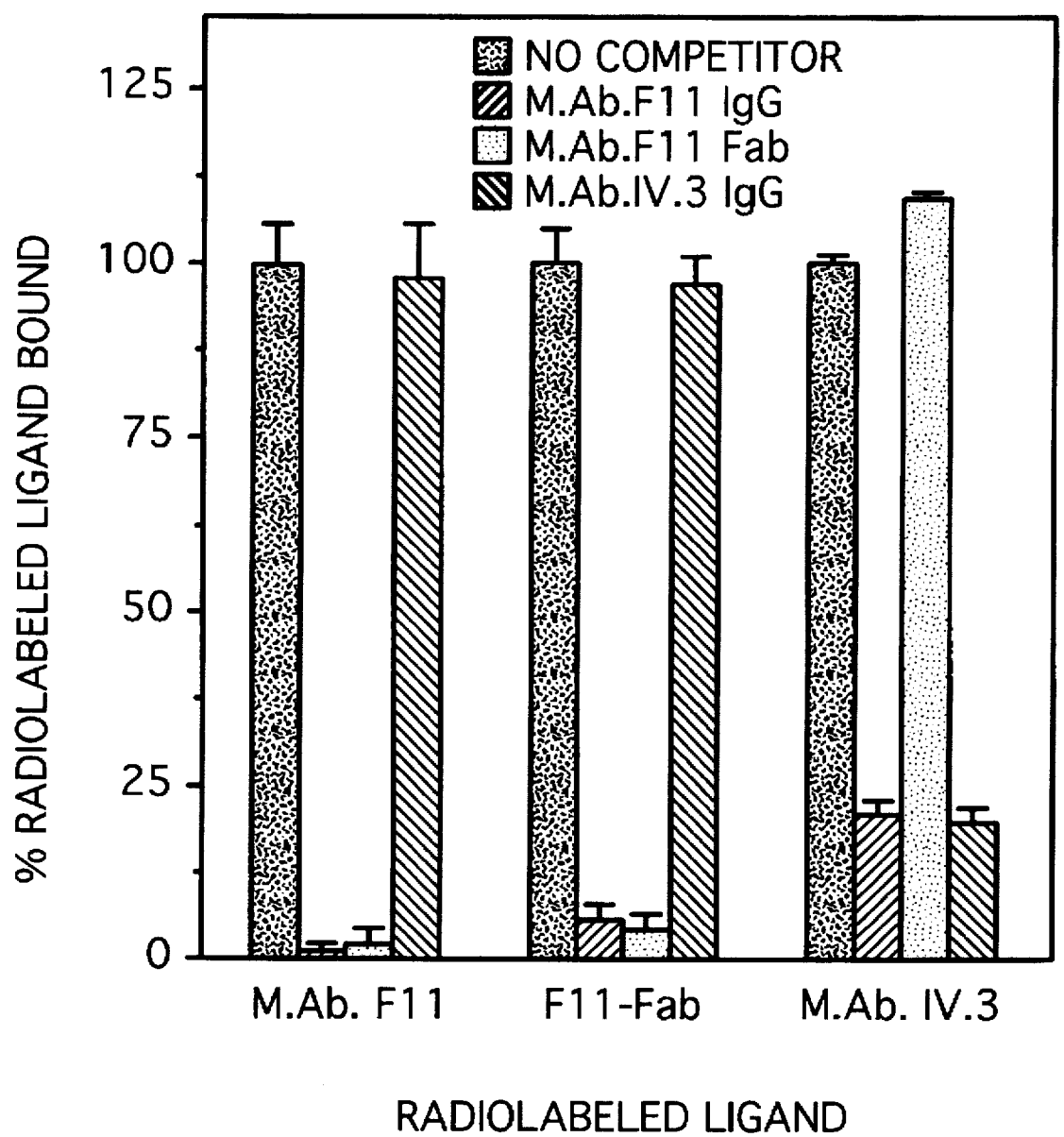
FIG. 12 shows the inhibition of the binding of M.Ab.F11 to washed platelets by M.Ab.IV.3.

Specific Binding of $^{125}$I-M.Ab.F11 and $^{125}$I-M.Ab.IV.3 to Platelets: FIG. 12 illustrates the lack of inhibition of radiolabeled M.Ab.F11 binding to washed platelets by M.Ab.IV.3. Fresh human platelet-rich plasma was incubated for 30 minutes at 37° C. with $^{125}$I-labeled M.Ab.F11 (2×10$^6$ cpm/ml), with $^{125}$I-Fab fragment of M.Ab.F11, or with $^{125}$I-M.Ab.IV.3. Displacement of binding of each ligand was studied by addition of either unlabeled M.Ab.F11 (10 µg/ml), unlabeled Fab fragment of M.Ab.F11 (200 µg/ml), or unlabeled M.Ab.IV.3 (10 µg/ml). Although the binding of $^{125}$I-M.Ab.F11 to platelets was specifically inhibited by the addition of non-labeled M.Ab.F11 (Table 1, FIG. 12) or its Fab fragments (FIG. 12), the binding of $^{125}$I-M.Ab.F11 was not inhibited by M.Ab.IV.3 (FIG. 12). Similarly, the binding of the m$^{125}$I-Fab fragment of M.Ab.F11 was inhibited by M.Ab.F11 and its Fab fragments, but such binding was not inhibited by M.Ab.IV.3 (FIG. 12). These results indicate that M.Ab.F11 (through its Fab domain) and M.Ab.IV.3 bind to two distinct receptors on the platelet surface. The binding of $^{125}$I-M.Ab.IV.3 was inhibited by the M.Ab.F11 IgG molecule (FIG. 12). Only intact M.Ab.F11, but not its Fab fragment, blocked the binding of M.Ab.IV.3 to its FcγRII receptor. This finding suggests that the Fc domain of the intact M.Ab.F11 IgG molecule interacts with the platelet Fc receptor and competes with the binding of M.Ab.IV.3 to the FcγRII receptor.

Figure 13:
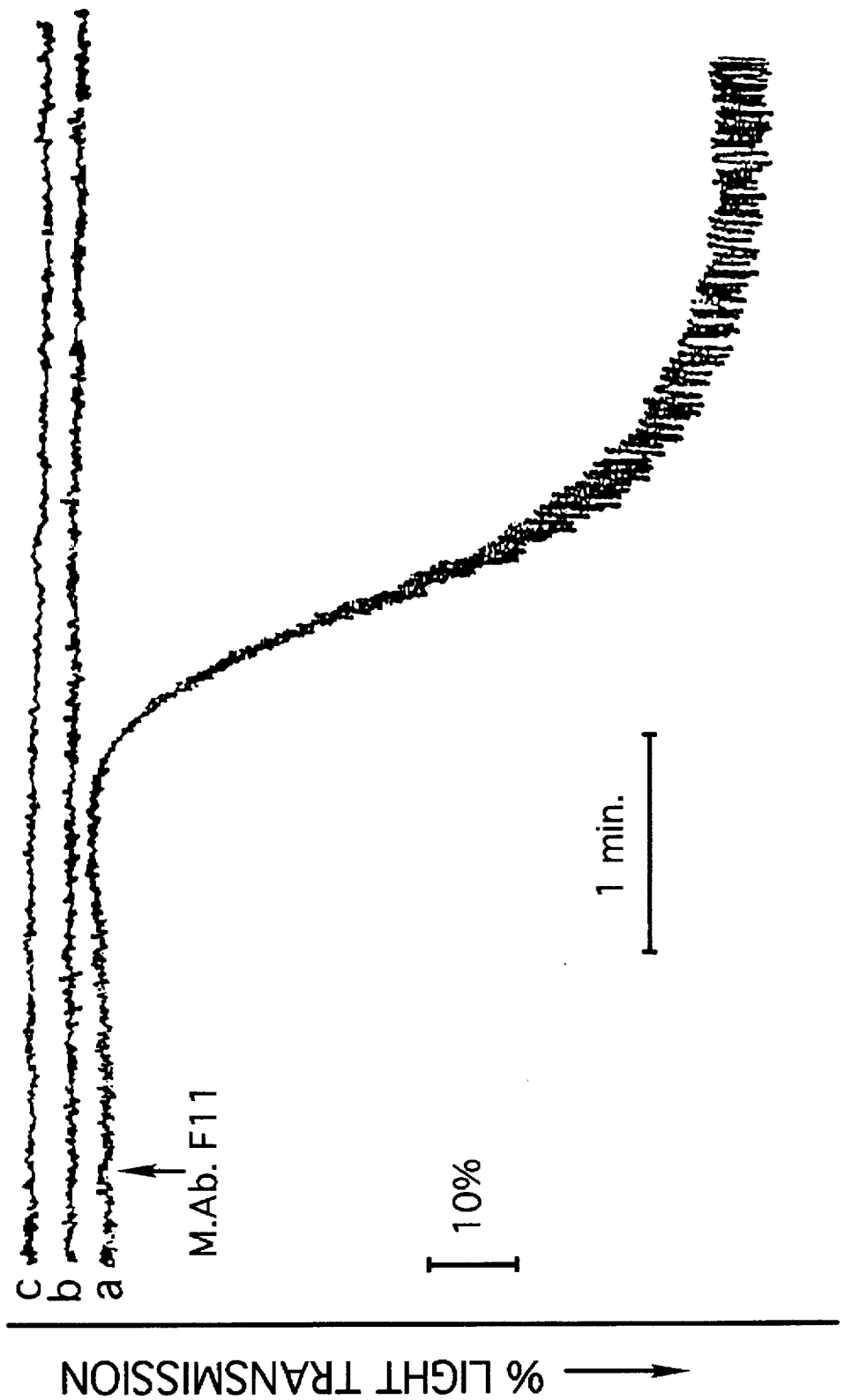
FIG. 13 shows the inhibition of M.Ab.F11-induced platelet aggregation by purified platelet membrane glycoprotein F11.

Effect of Purified F11 Receptor Protein on M.Ab.F11-Induced Platelet Aggregation: FIG. 13 illustrates the inhibition of M.Ab.F11-induced platelet aggregation by purified F11 receptor. In (a), platelet suspensions were stimulated by M.Ab.F11 (5 µg/ml) alone. In (b), platelet suspensions were incubated for 2 minutes at 37° C. with the purified F11 receptor protein (1 µg/ml) followed by the addition of M.Ab.F11. In (c), platelet suspensions received a simultaneous addition of a mixture of the M.Ab.F11/purified F11 receptor protein prepared exogenously as an immune complex. As shown, preincubation of platelet suspensions with the purified F11 receptor (1 µg/ml) resulted in inhibition of platelet aggregation induced by M.Ab.F11 (FIG. 13). Similarly, when M.Ab.F11 was exogenously added to the purified F11 receptor prior to its addition to platelets, such an immune complex failed to induce platelet aggregation and secretion (FIG. 13).

The mechanism by which monoclonal antibody F11 induces granule secretion and platelet aggregation was investigated in detail. M.Ab.F11 specifically recognizes two unique platelet membrane proteins of molecular weight 32 and 35 kD (the F11 receptor) (Kornecki et al., 1990). The F11 receptor is a unique platelet membrane protein in that its amino acid sequence differs from that of any known proteins (as detailed below) and it is not recognized by numerous other stimulatory antibodies which were unable to block the binding of $^{125}$I-M.Ab.F11 to intact platelets (Table 1). Both the Fab and Fc domains of the intact IgG molecule of M.Ab.F11 are required for the stimulation of platelets. The binding of radiolabeled $^{125}$I-M.Ab.F11 to its receptor occurs through the Fab domain since the binding of the intact IgG molecule was completely inhibited by isolated Fab but not Fc fragments. The Fab and F(ab')2 fragments alone do not stimulate platelet aggregation but they do inhibit the M.Ab.F11-induced activation of platelets.

The evidence that the Fc domain is essential for platelet aggregation by M.Ab.F11 is further substantiated by use of the FcγRII receptor antibody, IV.3. The M.Ab.F11-induced activation of platelets was completely blocked by preincubation of platelets with M.Ab.IV.3. M.Ab.IV.3 also blocked granular secretion induced by M.Ab.F11 as measured by inhibition of ATP and serotonin release. M.Ab.IV.3 was found to completely inhibit the M.Ab.F11-induced increase in the intracellular levels of free calcium ions and the enhanced intracellular phosphorylation of the 40 kD and 20 kD proteins, both events which were required for M.Ab.F11-induced secretion and aggregation. These findings directly demonstrate the involvement of the FcγR11 receptor in the pathway of signal transduction triggered by the binding of M.Ab.F11 to its own surface receptor. The inhibition by M.Ab.IV.3 of M.Ab.F11-induced secretion and aggregation was not due to its interference with the binding of M.Ab.F11 to its receptor since M.Ab.IV.3 did not block the binding of $^{125}$I-M.Ab.F11 or its Fab fragments to platelets. Since the intact M.Ab.F11 IgG molecule (but not Fab fragments) competitively inhibited the binding of radiolabeled M.Ab.IV.3 to the platelets, this inhibition was mediated through the Fc domain of M.Ab.F11. Furthermore, F11 receptor occupancy by M.Ab.F11 did not affect the number of FcγRII receptor binding sites since Fab fragments of M.Ab.F11 did not increase nor decrease the binding of M.Ab.IV.3 to its receptor.

Interaction of the IV.3 antibody alone with the platelet FcγRII receptor is not sufficient by itself to induce cellular activation. The platelet FcγRII receptor, a 40 kD molecule, has been shown to transduce a signal leading to platelet activation only when cross-linked by immune complexes or aggregated IgG (Rosenfeld et al., 1985; 1987). Platelet stimulation induced by anti-FcγRII receptor antibodies has been shown to occur only in those experiments in which two Fab fragments of M.Ab.IV.3 were crosslinked by F(ab')2 fragments of a secondary antibody (Worthington et al., 1990; Anderson and Anderson, 1990). Although the biochemical pathway by which FcγRII transduces a signal across the platelet plasma membrane is not well understood, these experiments indicate that cross-linking of two antigen molecules recognized by IV.3 on the platelet surface appear to trigger a signal transduction process. The results herein suggest another mechanism by which a stimulatory monoclonal antibody results in platelet aggregation, secretion and activation. The data demonstrates that platelet activation results from simultaneous interaction of the M.Ab.F11 molecule with both its own receptor (F11 receptor) and with the FcγRII receptor; the intact IgG molecule of M.Ab.F11 therefore produces a heterodimeric crosslink between the F11 receptor (32–35 kD protein duplex) recognized by its Fab domain of M.Ab.F11 and the FcγRII protein interacting with the Fc domain. This crosslinking is essential for platelet activation by the stimulatory antibody M.Ab.F11. The specific platelet surface proteins which are recognized by M.Ab.F11 (32 kD and 35 kD) appear to play an important and significant role in platelet function.

EXAMPLE 2
Experimental Procedures

Materials: PMSF, BSA, NP-40, Trisma base, $Me_2SO$, $PGE_1$, and apyrase grade V were purchased from Sigma Chemical Co. (St. Louis, MO). CNBr-activated Sepharose CL4B and DEAE-Sepharose were purchased from Pharmacia (Piscataway, NJ). Reagents for poly-acrylamide gel electrophoresis were obtained from BioRad (Melville, NY). All other reagents used were analytical grade.

Blood Collection: Blood was obtained from individuals who were free of any medication for at least two weeks prior to experimentation. Venous blood was collected into trisodium citrate (3.8%). Platelet-rich plasma was prepared by centrifugation at 200×g for ten minutes at 24° C.

Platelet Aggregation: The platelet aggregation experiments were carried out in a Chronolog lumi-aggregometer (Chronolog Corp., Haverstown, Pa.) as described above. Platelet-rich plasma (0.45 ml) was placed in a siliconized cuvette and aggregation was initiated by the addition of M.Ab.F11 (10 μg) with constant stirring at 1200 rpm at 37° C.

Washing of Outdated Platelets: Platelets were isolated from outdated platelet concentrates by centrifugation at 1200×g for ten minutes at 24° C. Platelets were then washed three times using Tyrode's-BSA (0.35%) solution buffered with 20 mM HEPES, 2 mM calcium chloride, 11.9 mM sodium bicarbonate, 0.36 mM sodium dihydrogen phosphate, 5.5 mM glucose, 1 mM magnesium chloride, 1 μM $PGE_1$, 1 unit/ml apyrase and 2 unit/ml of heparin, following the procedure of Mustard et al. (1972). Washed platelets were stored frozen at −70° C. until use.

F11 Receptor Protein Purification: The washed platelets ($2\times10^{11}$) were re-suspended in 200 ml of 20 mM tris-HCl buffer, pH 8.0, containing PMSF (2 mM), leupeptin (10 μg/ml), aprotinin (10 μg/ml), iodoacetemide (20 mM), benzamidine-HCl (5 mM) and soybean trypsin inhibitor (10 μg/ml) and subjected to pressure homogenization using the pressure homogenization technique (Hunter and Commerford, 1961). The plasma membranes were isolated by differential centrifugation. The membrane proteins were extracted in 1% NP-40 overnight at 4° C. After ultracentrifugation, the extract was diluted five fold with 20 mM Tris-HCl buffer (pH 8.0) containing protease inhibitors and then passed through a DEAE-Sepharose column pre-equilibrated with 20 mM Tris-HCl buffer (pH 8.0) containing 150 mM NaCl and 0.1% NP-40. The flow-through material contained all of the F11 antigen; this material was concentrated by ultrafiltration to its original volume and then applied onto a Sepharose CL-4B column to remove non specific binding. The material was then applied on a M.Ab.F11 affinity column obtained by coupling the M.Ab.F11 (5 mg/ml) to CNBr-activated Sepharose CL-4B. After extensive washing with Tris-HCl buffer (pH 8.0) containing 1 M NaCl and Tris-HCL buffer containing 0.5% sodium dioxycholate (pH 8.0) to remove nonspecific proteins, the bound F11 receptor protein was eluted by 50 mM diethylamine (pH 11.5) in 0.5% sodium dioxycholate. Fractions were collected into 1 M Tris (pH 8.0) and immediately dialyzed against 10 mM Tris-HCl (pH 7.4) containing sodium dioxycholate. The purification was monitored by Western blotting analysis using M.Ab.F11.

The M.Ab.F11 affinity column exhibited great sensitivity to changes in pH (pH 11.5 or pH 3.0). The instability of the M.Ab.F11 column was evident following a single regeneration period. In contrast, the use of another monoclonal antibody (M.Ab. G10), directed against platelet glycoprotein IIIa, when coupled to CnBr-activated Sepharose, did not exhibit such instability. The M.Ab.G10 column was stable to both high pH (pH 11.5) and low pH (pH 3.0) following its regeneration.

Amino Acid Sequencing: The affinity purified receptor protein was separated by 5–15% SDS-Polyacrylamide gels and transferred to polyvinylidene difluoride (PVDF) membrane (Matsudaira, 1987). The proteins were stained by 0.1% Ponceau S in 1% acetic acid. The F11 receptor band corresponding to 32 kD was excised and sequenced using ABI 470 A gas-phase protein sequencer, equipped with 900 A data acquisition system. The receptor band from PVDF membrane was also proteolytically digested with endoproteinase Glu-C trypsin, and endoproteinase Lys-C obtained from Boehringer Mannheim (Indianapolis, IN). Ponceau S-stained bands (5 μg of protein) were de-stained by 0.5 ml of 200 mM NaOH in 20% acetonitrile for one minute. The remaining non-specific binding sites were blocked with 0.2% PVP-40 in methanol. Samples were digested in the presence of 1% hydrogenated Triton X-100 in 10% acetonitrile in 100 mM Tris-HCl, pH 8.0 by trypsin (0.1 μg of enzyme/μg of substrate protein), endoproteinase Glu-C (0.1 μg of enzyme/μg of substrate) or endoproteinase Lys-C (0.0075U/μg substrate). Digestions were carried out at 37° C. for twenty-four hours. Following digestion, samples were sonicated for five minutes and then centrifuged. The supernatants containing the digested peptides were analyzed by HPLC. The endoproteinase Lys-C failed to digest the protein, but endoproteinase Glu-C and trypsin gave a distinct peptide profile. The endoproteinase Glu-C and trypsin-derived peptides were separated on a 1090 M microbore HPLC (Hewlett Packard, Wilmington, DE) using Vydac C18-reverse phase column (2.1×250 mm) with a flow rate of 150 μl/minute and peptide elution was monitored at 220 nm. Seventy-five μl fractions were collected and used for sequence analysis.

Iodination of Antibodies and Antibody Binding to Platelets: Purified monoclonal antibodies and their Fab fragments were radiolabeled by using the method of Iodo-Beads as described previously. The specific activities were approximately $2\times10^7$ cpm/μg when 50 μg/ml of monoclonal antibodies were radiolabeled by this method. Binding of radiolabeled antibodies to platelets in plasma or to washed platelets was performed over a 200 μl cushion of 20% sucrose. The incubation mixture consisted of 90 μl of platelet aliquots ($2-5\times10^8$ platelets/ml) and radiolabeled monoclonal antibodies in a total volume of 100 μl.

SDS-PAGE: SDS-PAGE was performed in 3% stacking gels and in 5–15% gradient separation polyacrylamide slab gels according to the procedure of Laemmli (1970). The gels were stained for proteins with Coomassie Brilliant Blue, de-stained in 10% acetic acid, 20% methanol, dried in vacuo, and exposed to Kodak X-Omat AR film with Dupont-Cronex Lightning Plus intensifying screens for approximately one to two hours at −70° C. and developed in a Kodak X-Omar developer (Eastman Kodak Company, Rochester NY). Molecular weight determinations were made by comparison to Bio-Rad reduced samples of myosin (200,000), *Escherichia coli* β-galactosidase (116,000), phosphorylase b (97,400), bovine serum albumin (66,200), ovalbumin (42,700), carbonic anhydrase (31,000), soybean trypsin inhibitor (21,500), and lysozyme (14,400).

Figure 14:
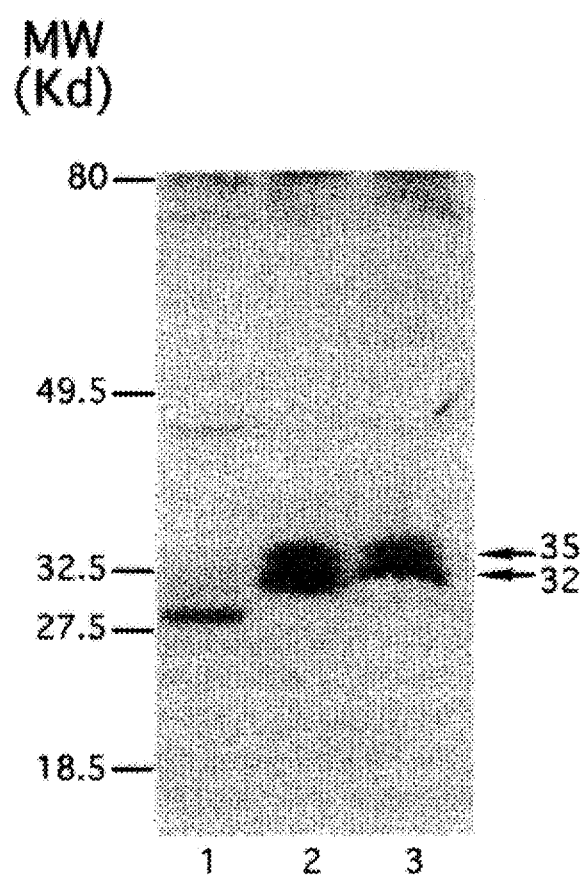
FIG. 14 is an immunoblot showing the 32 kD and 35 kD receptor proteins of the duplex forming the F11 receptor.

Post-translational modification of F11 receptor protein: Stimulatory monoclonal antibody M.Ab.F11 induces human platelet activation leading to granular secretion and platelet aggregation. M.Ab.F11 specifically recognizes a duplex of platelet membrane proteins of molecular weight 32 and 35 kD (FIG. 14, lane 2). In order to determine whether these proteins have the same antigenic epitope or are two forms of the same protein resulting from post translational modification, the partially purified proteins were digested with N-glycanase and O-glycanase. Partially purified F11 receptor proteins (32 and 35 kD) were digested overnight at 37° C. with N-glycanase (lane 1), with O-glycanase (lane 3), and without any enzyme (control, lane 2). The F11 receptor proteins were separated by SDS-PAGE and immunoblotted using M.Ab.F11 and goat anti-mouse alkaline phosphatase conjugate as second antibody. As seen in FIG. 14, the undigested proteins showed a duplex of 32 and 35 kD (FIG. 14, lane 2). O-glycanase had no effect on these proteins (FIG. 14 lane 3), whereas, N-glycanase converted the two proteins into a single protein band of 29 kD. These results suggest that the 32 and 35 kD F11 antigen in fact are derived from a single core protein by differential glycosylation.

Figure 15:
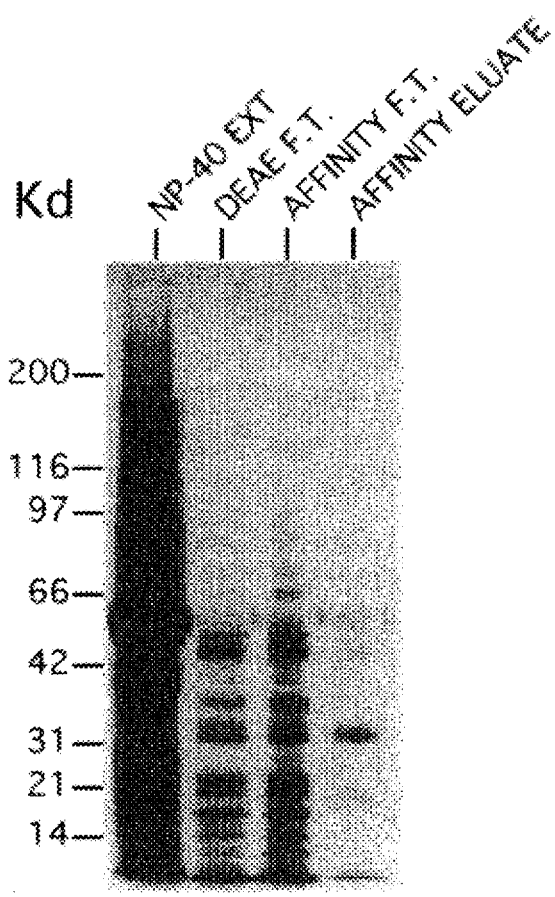
FIG. 15 is an immunoblot showing the purification pattern of the F11 receptor protein.
Figure 16:
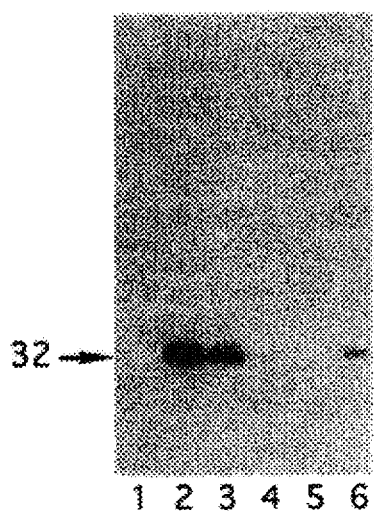
FIG. 16 is an immunoblot of the samples of each step of purification.

Purification of F11 Receptor: Using $^{125}$I-labeled M.Ab.F11, it was determined that outdated platelets from a blood bank can serve as an excellent source of material for the purification of the F11 receptor antigens. The 32 kD was the major form of the F11 receptor present in washed outdated platelets, with smaller amounts of 35 kD, in contrast to the near equal intensity of the two forms in fresh platelets. The purification steps are summarized in Table 2. The purification pattern of the F11 receptor protein is shown in FIG. 15, which illustrates the silver staining of the proteins separated by a 5–15% gradient on SDS-PAGE (NP-40 extract 500 µg; DEAE F.T. 20 µg; Affinity F.T. 20 µg; and Affinity eluate 100 ng were applied to the gel). FIG. 16 is an immunoblot of the samples at each step of purification. In the immunoblot of the proteins separated by SDS-PAGE, lane 1 represents 200 µg of cytosol; lane 2 represents 20 ng of affinity eluate; lane 3 represents 100 µg of DEAE flow-through; lane 4 represents 100 µg of affinity pass-through; lane 5 represent 200 µg DEAE eluate; and lane 6 represents 500 µg of NP-40 extract.

Membrane and cytosol proteins were prepared from $2\times10^{12}$ platelets in the presence of proteinaceous inhibitors. Immunoblotting with M.Ab.F11 showed that all the F11 antigen was associated with the membrane fraction. The membrane proteins were extracted with 1% NP-40. The detergent extract had 21% of the total proteins (Table 2, FIG. 15, lane 1) but showed 100% of the detectable F11 antigen as seen by immunoblotting (FIG. 16). The NP-40 extract had large amounts of proteins including myosin, actin, GPIIb and GPIIIa. Actin and myosin were found to be major contaminants in the immunoaffinity chromatography. The NP-40 extract was subjected to DEAE ion exchange chromatography. The salt conditions (150 mM NaCl) and pH (8.0) of the equilibrating buffer were selected so that the F11 antigen would pass through the DEAE column, whereas albumin, actin, myosin, GPIIb, and GPIIIa would remain bound to the DEAE column (FIG. 15, lane 2); these proteins could be eluted by use of buffer containing 0.5 M NaCl. This purification step resulted in a 97% yield of the F11 antigen as determined by immunoblotting (FIG. 16, lane 3) and only 8% of the total proteins (Table 2).

The M.Ab.F11, when coupled to cyanogen bromide-activated Sepharose, was used in the final step of purification. The DEAE flow-through material was passed over a 5 ml M.Ab.F11 affinity column with a 2 ml/minute flow rate. The column was then extensively washed with 1000 ml each of 1 M NaCl and 0.5% Deoxycholate to remove the non-specific binding, and the F11 antigen was eluted using 50 mM diethylamine (pH 7.5) in 0.5% deoxycholate. The yield was a total of 24.8 µg of the F11 antigen with a yield of 82% (Table 2, FIG. 15 and FIG. 16, lane 2). A $4.1\times10^7$ fold purification was achieved. As seen from FIG. 15 and FIG. 16, the purified F11 receptor contained the 32 kD protein a major form; smaller amounts of the 35 kD protein were also obtained.

Figure 17:
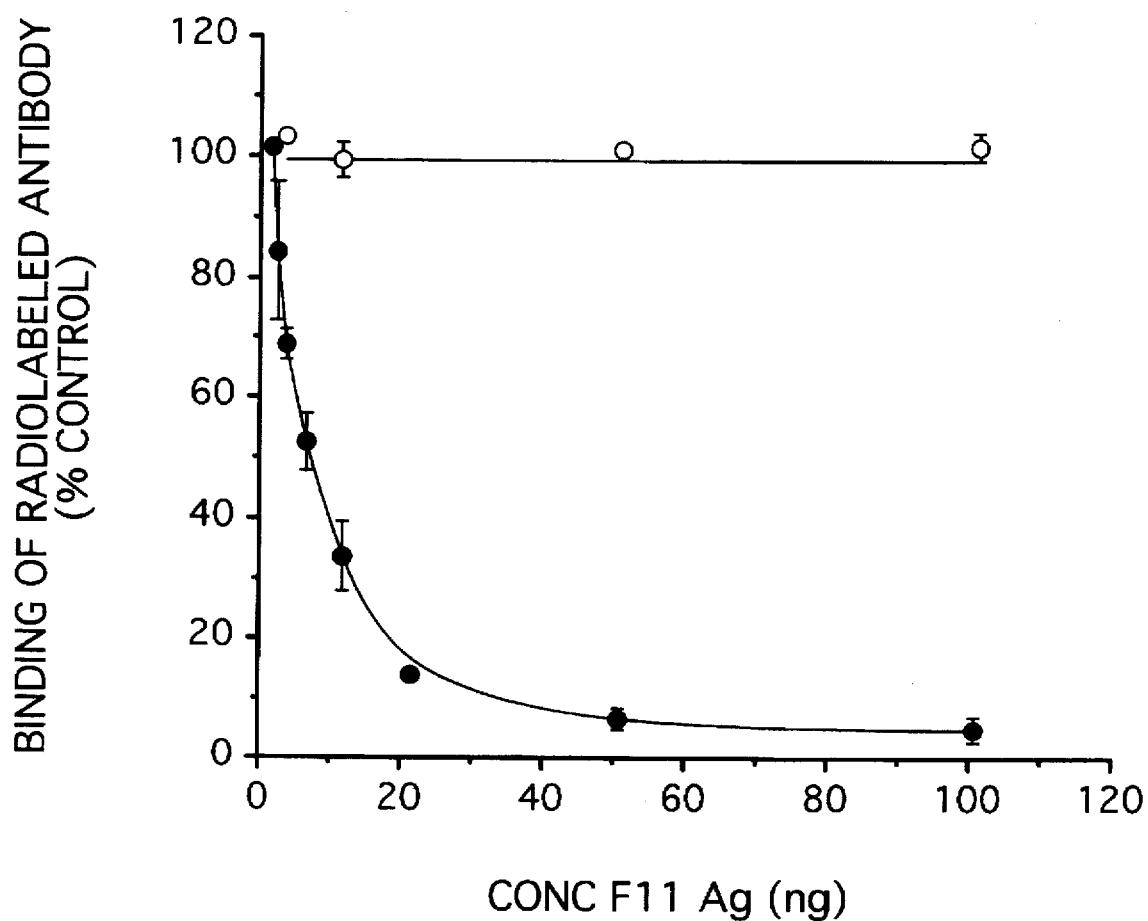
FIG. 17 shows the inhibition of M.Ab.F11 binding to the platelet by purified F11 receptor.

In order to further confirm that the purified protein was in fact the active antigen, inhibition of M.Ab.F11-induced platelet aggregation by purified F11 receptor was examined. Referring to FIG. 13, platelet suspensions ($3\times10^8$ platelets/ml) were incubated either without (a), or with (b), the purified F11 receptor for 2 minutes prior to the addition of M.Ab.F11. The aggregation response was monitored using a lumi-aggregometer. The preincubation of the purified F11 antigen with platelet suspensions inhibited the aggregation induced by M.Ab.F11. FIG. 17 shows the dose-dependent inhibition of the binding of $^{125}$I-labeled M.Ab.F11 to the fresh platelets by the addition of purified F11 receptor protein. Platelet suspensions ($3\times10^8$ platelets/ml) were incubated with various concentrations of the purified F11 receptor protein. After 2 minutes of incubation at 37° C., $^{125}$I-labeled antibodies were added and incubated for another 30 minutes. Specific binding was quantitated after separating the bound from the free ligand by centrifugation over 20% sucrose cushion. Referring to FIG. 17, the purified F11 protein was able to completely inhibit the binding of M.Ab.F11 (darkened circle) to intact platelets with an $IC_{50}$ value of 6.0 ng. However, 100 ng of this protein failed to inhibit the binding of a $^{125}$I-labeled monoclonal antibody M.Ab.G10 (open circle); M.Ab.G10 is specific to GPIIIa. M.Ab.G10 was used as a control in these experiments.

Figure 18:
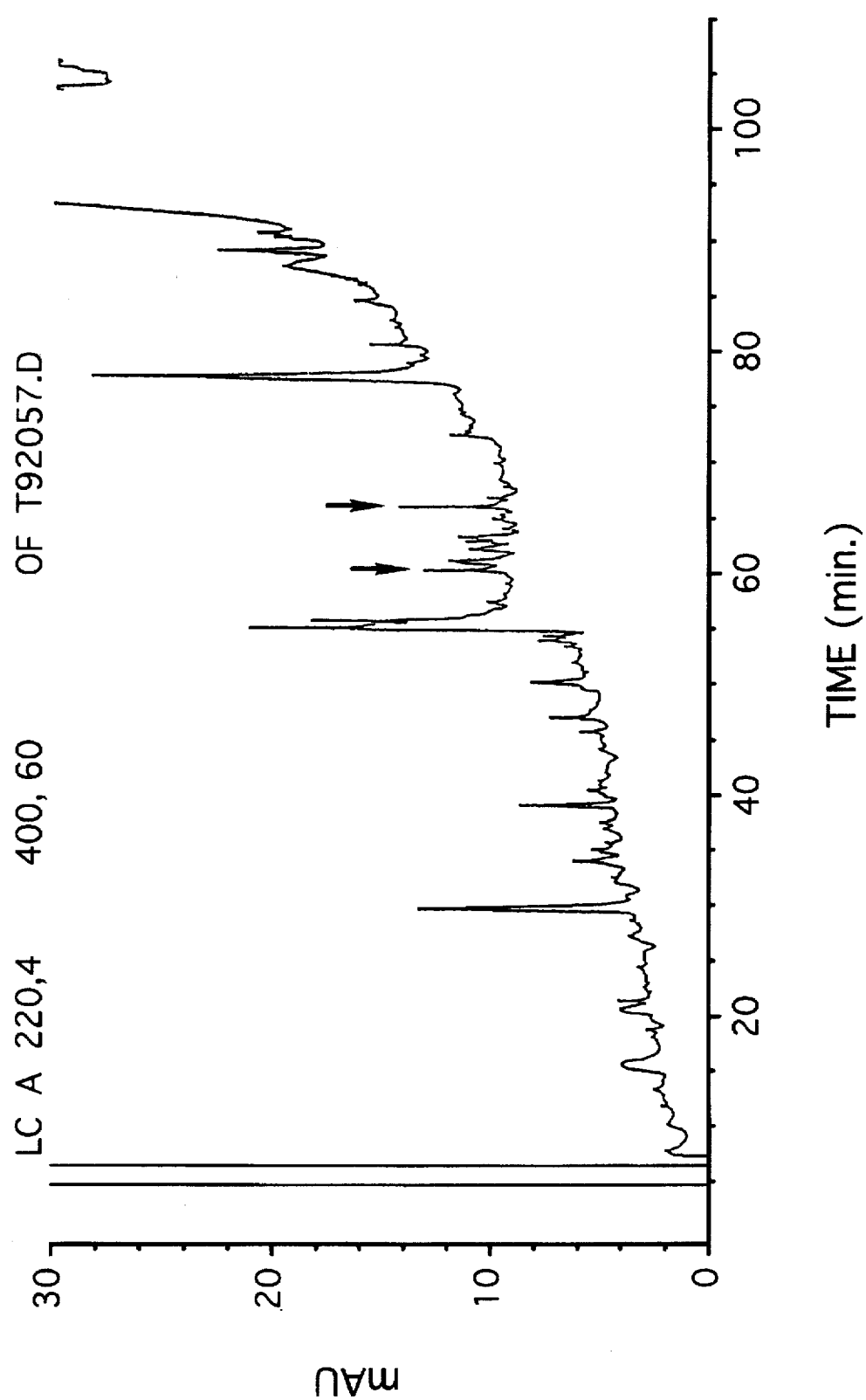
FIG. 18 shows the HPLC elution profile of the peptides derived from the F11 receptor protein following digestion with trypsin.
Figure 19:
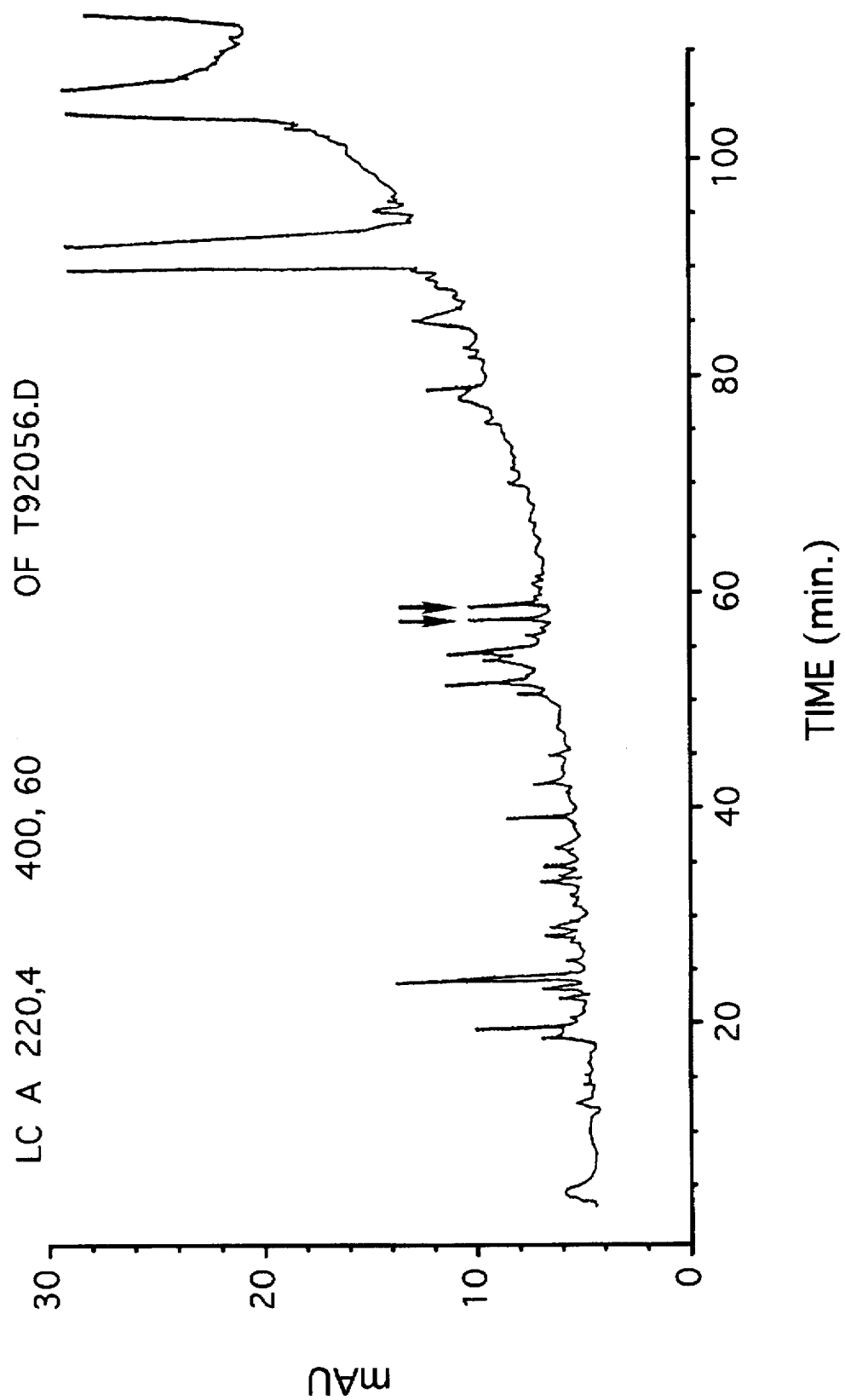
FIG. 19 shows the HPLC elution profile of the peptides derived from the F11 receptor protein following digestion with proteinase Glu-C.

Amino Acid Sequencing of the F11 Antigen receptor protein: FIGS. 18 and 19 illustrate the HPLC elution profiles of the peptides derived from F11 receptor protein following digestion with trypsin (FIG. 18) and proteinase Glu-C (V8 Protease) (FIG. 19). Arrows indicate the peptides used for internal amino acid sequencing. The N-terminal amino acid sequence of the 32 kD form of the F11 antigen was determined as described in the experimental conditions. A 34 amino acid sequence at the N-terminal corresponding to SEQ ID NO: 1 was obtained. Referring to Table 3, the probable amino acids at the Xaa positions are given in order of likelihood. The most likely amino acid represents the major peak, and the other possible amino acids at a given position represent minor peaks. The sequence of the N-terminal 34 amino acids as determined from the major peaks corresponds to:

| SEQ ID NO:8: |
| --- |
| Ser Val Thr Val His Ser Ser Glu Pro Glu Val Arg Ile Pro Glu Asn Asn Pro Val Lys Leu Ser Cys Ala Tyr Gly Met Phe Gln Xaa Pro Xaa Ser Gly. |

The N-terminal peptide was highly hydrophilic as determined by Kyte-Dolittle hydropathy analysis. The 34-amino acid N-terminal sequence obtained was searched for any homology to known proteins reported in Swiss PROT database. The N-terminal amino acid sequence exhibited a small degree of identity to the T-cell receptor; a 46% identity to the 12 to 45 amino acid region of the N terminal variable region of the s-chain of the human T-cell receptor.

In contrast to the N-terminal sequence of the F11 receptor, the internal amino acid sequences of the F11 receptor (see Table 3, SEQ ID NOs:2–7) do not contain any regions of homology to the T-cell receptor nor to any other known proteins; the above-mentioned information demonstrates that the F11 antigen is a unique and novel protein. The internal amino acid sequences corresponding to SEQ ID NOs: 2–7 are presented in Table 3. As with the 34 amino acid N-terminal sequence, the probable amino acids at the Xaa positions are given in order of likelihood. The internal amino acid sequence as determined from the major peaks for SEQ ID NO:2 corresponds to SEQ ID NO:9: Phe Asp Lys Asp Xaa Thr Ile Tyr Leu Ash Xaa Tyr. The internal amino acid sequence corresponding to SEQ ID NO:3 represents the amino acid sequence as determined from the major peaks. The internal amino acid sequence as determined from the major peaks for SEQ ID NO:4 corresponds to SEQ ID NO:10:

Asp Arg Val Thr Phe Leu Pro Thr Gly Ile Thr Phe Lys
Ser Val Thr Arg Glu.

The internal amino acid sequence as determined from the major peaks for SEQ ID NO:5 corresponds to SEQ ID NO:11:

Trp Lys Phe Asp Gln Gly Asp Thr Thr Arg Leu Val Glu
Tyr Asn Asn Lys Ile Thr Ala Ser Tyr Glu Asp Arg Val
Thr Phe Leu Pro Thr Gly Ile Thr Phe Lys Ser Val Thr
Arg Glu Asp Xaa Gly Gln Tyr Leu Asp Met Asp.

The internal amino acid sequence as determined from the major peaks for SEQ ID NO:6 corresponds to SEQ ID NO:12: Val Thr Phe Leu Pro Thr Gly Ile Thr Phe Lys. The internal amino acid sequence as determined from the major peaks for SEQ ID NO:7 corresponds to SEQ ID NO:13: Leu Thr Asp Xaa Gly Gln.

When the isolated peptides were analyzed by Prosite computer program for the consensus sequence for any phosphorylation site, the N-terminal peptide was found to exhibit a putative phosphorylation site for casein kinase II whereas the internal peptides obtained by trypsin or Glu-C digestion exhibited putative phosphorylation sites for protein kinase C (PKC) (Table 3).

Phosphorylation of the F11 Receptor: The F11 antigen has a consensus site for phosphorylation by PKC. To examine whether PKC is involved in the phosphorylation of the F11 receptor, the purified F11 receptor protein was incubated (using a procedure that included M.Ab.F11 chromatography but didn't include DEAE chromatography) with $[\gamma^{32}P]ATP$, $Ca^{++}$ and phosphotidyl serine in the presence of TPA (FIG. 20).

Figure 20:
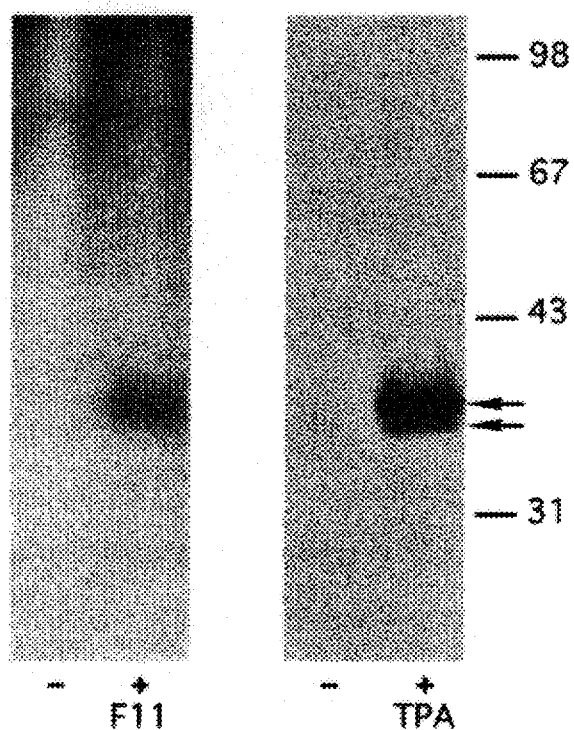
FIG. 20 is an autoradiogram showing the phosphorylation of the F11 antigen.

As seen in FIG. 20, the addition of M.Ab.F11 resulted in the phosphorylation of the F11 receptor. Similar phosphorylation of the F11 receptor protein occurred in the presence of TPA, to a much greater extent than with M.Ab.F11. This indicates that the F11 affinity-purified preparation contains a F-11 receptor which is associated with PKC capable of phosphorylating the F11 receptor. In contrast, when the DEAE ion exchange chromatography step was introduced before affinity purification, then M.Ab.F11 or TPA addition failed to result in the phosphorylation of the F11 receptor.

These results suggest that the F11 receptor is associated with a complex that contains a PKC capable of causing ligand-induced receptor phosphorylation. This kinase could be separated from the receptor complex by DEAE ion chromatography.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Lack of inhibition of binding of $^{125}$I-M.Ab.F11 to human platelets in the presence of various antibodies against CD9 antigen.

| Antibody tested[a] | Isotype | % of control |
|---|---|---|
| Control[b] | — | 100 ± 1.3 |
| M.AB.F11[c] | IgG$_1$ | 3 ± 2.1 |
| PTA1[c] | IgG$_{2a}$ | 101 ± 3.8 |
| P1/33/2C[c] | IgG$_{2a}$ | 93 ± 4.1 |
| 15C3[c] | IgG$_1$ | 91 ± 3.6 |
| AG-1[c] | IgG$_1$ | 100 ± 0.8 |
| alb-6[c] | IgG$_1$ | 113 ± 3.2 |
| MM/57[c] | IgG$_{2b}$ | 110 ± 2.8 |
| H19A[d] | IgG$_1$ | 100 ± 2.0 |
| GR2110[d] | IgG$_{2a}$ | 103 ± 1.6 |

[a] Antibodies submitted for the 5th International Workshop and Conference on Human Leukocyte Differentiation Antigens, November 3–7, 1993, Boston, MA, USA.
[b] In control samples, an equal volume of TBS (pH 7.4, 10 µl) was added.
[c] Purified IgG was used at a final concentration of 0.1 mg/ml.
[d] Ascites fluid was used at a 1:10 dilution.

TABLE 2

Purification of F11 Receptor Protein

| Purification Steps | Total Protein | % Protein Recovery | % F11 Antigen Recovery[+] | Fold Purification |
|---|---|---|---|---|
| Platelets (2 × 10$^{12}$) | — | — | — | — |
| Homogenate | 11.9 g | 100 | 100 | 1 |
| NP40 Extract | 2.495 g | 20.97 | 97 | 4.6 |
| DEAE Flow through | 960 mg | 8.07 | 90 | 11.2 |
| Affinity eluate | 24.8 µg* | 2.0 × 10$^{-6}$ | 82 | 4.1 × 10$^7$ |

*Protein estimation by silver staining.
[+]Estimated from the immunoblott by densitometry.

TABLE 3

Amino Acid Sequences of Peptides Derived from F11 Receptor Protein

| Peptide | Amino acid sequence | Phosphorylation site |
|---|---|---|
| N-terminal | SEQ ID NO:1:<br>(P)<br>$^1$XVTVHSSEPEVRIPENNPVKL$^{22}$X$^{23}$XAY$^{26}$X$^{27}$XFQ$^{30}$XP$^{32}$XS$^{34}$X<br>$^1$X = S >> T, H > D, G, A<br>$^{22}$X = S, T<br>$^{23}$X = C<br>$^{26}$X = G > S<br>$^{27}$X = M, N<br>$^{34}$X = G, H<br>most probable = SEQ ID NO:8:<br>SVTVHSSEPEVRIPENNPVKLSCAYGMFQXPXSG | Casein kinase II |
| GLU-C DIGESTION | 1) SEQ ID NO:2:<br>$^1$X$^2$X$^3$X$^4$X$^5$XTIYL$^{10}$X$^{11}$XY<br>$^1$X = F > P<br>$^2$X = D > V<br>$^3$X = K, Q<br>$^4$X = D, N<br>$^{10}$X = N, T, V<br>most probable = SEQ ID NO:9:<br>FDKDXTIYLNXY<br>2) SEQ ID NO:3:<br>KFKLIVLV<br>3) SEQ ID NO:4:<br>(P)<br>D$^2$X$^3$X$^4$X$^5$X$^6$X$^7$X$^8$X$^9$XITFKSVTR$^{18}$X<br>$^2$X = R > K<br>$^3$X = V > F<br>$^4$X = T > K<br>$^5$X = F > L<br>$^6$X = L > I<br>$^7$X = P > V<br>$^8$X = T > L<br>$^9$X = G > V<br>$^{18}$X = E, I<br>most probable = SEQ ID NO:10:<br>DRVTFLPTGITFKSVTRE<br>4) SEQ ID NO:5:<br>$^1$X$^2$X$^3$X$^4$X$^5$X$^6$X$^7$X$^8$X$^9$X$^{10}$X$^{11}$X$^{12}$X$^{13}$X$^{14}$X$^{15}$X$^{16}$X$^{17}$X$^{19}$X$^{20}$X$^{21}$X$^{22}$X$^{23}$X$^{24}$X$^{25}$X$^{26}$X$^{27}$X$^{28}$XL$^{30}$X<br>$^{31}$X$^{32}$X$^{33}$X$^{34}$X$^{35}$XKSVTRED$^{43}$XG$^{45}$X$^{46}$XLDM$^{50}$X<br>$^1$X = W >> N, A<br>$^2$X = K >> N, V<br>$^3$X = F >> P, E > D<br>$^4$X = D >> V, R > T, L, I, Y<br>$^5$X = Q >> K, E, N > H, A<br>$^6$X = G >> V, L, D > S, T, R, P, W, I<br>$^7$X = D >> S<br>$^8$X = T > V > Y<br>$^9$X = T > A, I<br>$^{10}$X = R >> Y, V > N, P > F<br>$^{11}$X = L >> A, S > N, I<br>$^{12}$X = V >> G > Q, X, K<br>$^{13}$X = E, S<br>$^{14}$X = Y >> N, L<br>$^{15}$X = N >> D > G<br>$^{16}$X = N >> p<br>$^{17}$X = K >> R, L<br>$^{19}$X = T >> E, L<br>$^{20}$X = A >> N<br>$^{21}$X = S >> G > Y<br>$^{22}$X = Y >> F, I > Q<br>$^{23}$X = E >> L > D<br>$^{24}$X = D >> Q<br>$^{25}$X = R >> F > N<br>$^{26}$X = V > G<br>$^{27}$X = T > I<br>$^{28}$X = F > K<br>$^{30}$X = P > A<br>$^{31}$X = T > Y<br>$^{32}$X = G > S<br>$^{33}$X = I > R<br>$^{34}$X = T >> N<br>$^{35}$X = F >> N, H<br>$^{43}$X = cys or glycosylated residue | Protein kinase C |

TABLE 3-continued

Amino Acid Sequences of Peptides Derived from F11 Receptor Protein

| Peptide | Amino acid sequence | Phosphorylation site |
|---|---|---|
| | $^{45}$X = P, T<br>$^{46}$X = Y > S<br>$^{50}$X = V, R, N, D<br>most probable SEQ ID NO:11:<br>WKFDQGDTTRLVEYNNKITASYEDRVTFLPTGITFKSVRREDXGQYLDMD | |
| TRYPSIN DIGESTION | | |
| | 1) SEQ ID NO:6:<br>(P)<br>$^1$XTFLPTGITFK<br>$^1$X = V, S<br>most probable = SEQ ID NO:12:<br>VTFLPTGITFK<br>2) SEQ ID NO 7:<br>L$^2$XD*X$^5$X$^6$X<br>$^2$X = T, I<br>$^5$X = G, E<br>$^6$X = Q, V<br>most probable = SEQ ID NO:13:<br>LTDXGQ | Protein kinase C |

List Of References Cited

Anderson, G. and Anderson, C. L., Blood 76: 5–1172 (1990).
Boucheix, C. et al., FEBS 161:289–295 (1983).
Boucheix, C. et al., J Biol Chem 266:117–122 (1991).
Coller, B. S. et al., Blood 61:99–110 (1983).
Collet, B. S. et al., Blood 68:783–786 (1986).
Cosgrove, L. J. et al., Immunol Cell Biol 66:69–77 (1988).
Duncan, J. R. and Rosse, W. F., Brit J Haematol 64:331–338 (1986).
Gorman, E. J. et al., Nouv Fev Fr Hematol 27:255–259 (1985).
Handa, M. et al., J Biol Chem 261:12579–12585 (1986).
Higashihara, M. et al., Blood 65:382–391 (1985).
Hunter, M. J. and Commerford, S. L., Biochim Biophys Acta 47:580–586 (1961).
Jones, N. H. et al., Leuk Res 6:449–464 (1982).
Kersey, J. H. et al., J Exp Med 153:726–731 (1981).
Komada, Y. et al., Leuk Res 1:499–507 (1983).
Kornecki, E. and Feinberg, H., Am J Physiol 238:H54-H60 (1980).
Kornecki, E. et al., Thrombosis Research 34:35–49 (1984).
Kornecki, E. and Ehrlich, Y. H., Science 240:1792–1794 (1988).
Kornecki, E. et al., J Biol Chem 265:10042–10048 (1990).
Laemmli, U. K., Nature 227:680–685 (1970).
Lanza, R. et al., J Biol Chem 266:10638–10645 (1991).
Maniatis et al., Molecular Cloning: A Laboratory Manual, Cold Springs Laboratory, Cold Springs Harbor, New York (1982).
Matsudaira, P., J Biol Chem 262:10035–10038 (1987).
Modderman, P. W. et al., Thromb Haemost 60:68–74 (1988).
Morel, M. C. et al., Brit J Haematol 71:57–63 (1989).
Mustard, J. F. et al., J Haematol 22:193–204 (1972).
Naik, U. P. et al., Biochim Biophys Acta 1092:256–264 (1991).
Peters, A. M. et al., Brit Med J 293:1525 (1986).
Roberts and Lauer, Methods in Enzymology 68:473 (1979).
Rosenfeld, S. L. et al., J Clin Invest 76:2317–2322 (1985).
Rosenfeld, S. L. et al., J Immunol 138:2869–2873 (1987).
Ryu, T. et al., FASEB J 3:A312 (1989).
Scott, J. L. et al., J Biol Chem 264:13475–13482 (1989).
Studier, F. W. et al., Gene Expression Technology 185 (1990).
Thiagarajan, P. et al., Amer J Hematol 14:255–269 (1983).
Walkowiak, B. et al., Thromb Res 68:323–331 (1992).
Worthington, R. E. et al., Br J Haematol 74:216–222 (1990).
Yamaguchi, A. et al., Thromb Res 44:165–174 (1986).
Yanabu, M. et al., Brit J Haematol 78:87–93 (1991).

What is claimed is:

1. A purified platelet membrane glycoprotein designated F11.

2. A composition comprising the platelet membrane glycoprotein of claim 1 and a suitable carrier.

3. A pharmaceutical composition comprising an amount of the platelet membrane glycoprotein of claim 1 effective to inhibit platelet aggregation and a pharmaceutically acceptable carrier.

4. The platelet membrane glycoprotein of claim 1 further comprising a thrombolytic agent bound to said platelet membrane glycoprotein.

5. A purified platelet membrane glycoprotein designated F11 having an amino acid sequence which contains amino acid sequences:

---
SEQ ID NO:8:

Ser Val Thr Val His Ser Ser Glu Pro Glu Val Arg Ile Pro Glu Asn Asn Pro Val Lys Leu Ser Cys Ala Tyr Gly Met Phe Gln Xaa Pro Xaa Ser Gly;

SEQ ID NO:9:

Phe Asp Lys Asp Xaa Thr Ile Tyr Leu Asn Xaa Tyr;

SEQ ID NO:3:

Lys Phe Lye Leu Ile Val Leu Val;

SEQ ID NO;10:

Asp Arg Val Thr Phe Leu Pro Thr Gly Ile Thr Phe Lys Ser Val Thr Arg Glu;

SEQ ID NO:11:

Trp Lys Phe Asp Gln Gly Asp Thr Thr Arg Leu Val Glu Tyr Asn Asn Lye Ile Thr Ala Ser Tyr Glu Asp Arg Val Thr Phe Leu Pro Thr Gly Ile Thr Phe Lys Ser Val Thr Arg Glu Asp Xaa Gly Gln Tyr Leu Asp Met Asp;

SEQ ID NO:12:

Val Thr Phe Leu Pro Thr Gly Ile Thr Phe Lys; and

SEQ ID NO:13:

Leu Thr Asp Xaa Gly Gln,

--- wherein Xaa at amino acid residue 43 of SEQ ID NO:11 is selected from the group consisting of a Cys and a glycosylated residue.

6. A composition comprising the platelet membrane glycoprotein of claim 5 and a suitable carrier.

7. A pharmaceutical composition comprising an amount of the platelet membrane glycoprotein of claim 5 effective to inhibit platelet aggregation and a pharmaceutically acceptable carrier.

8. The platelet membrane glycoprotein of claim 5 further comprising a thrombolytic agent bound to said platelet membrane glycoprotein.

9. A purified platelet membrane glycoprotein designated F11 having an amino sequence which contains:

---
SEQ ID NO:8:

Ser Val Thr Val His Ser Ser Glu Pro Glu Val Arg Ile Pro Glu Asn Asn Pro Val Lys Leu Ser Cys Ala Tyr Gly Met Phe Gln Xaa Pro Xaa Ser Gly.

---

10. A purified platelet membrane glycoprotein designated F11 having an amino acid sequence which contains:

SEQ ID NO:9: Phe Asp Lys Asp Xaa Thr Ile Tyr Leu Asn Xaa Tyr.

11. A purified platelet membrane glycoprotein designated F11 having an amino acid sequence which contains:

SEQ ID NO:3: Lys Phe Lys Leu Ile Val Leu Val.

12. A purified platelet membrane glycoprotein designated F11 having an amino acid sequence which contains:

---
SEQ ID NO:10:

Asp Arg Val Thr Phe Leu Pro Thr Gly Ile Thr Phe Lys Ser Val Thr Arg Glu.

---

13. A purified platelet membrane glycoprotein designated F11 having an amino acid sequence which contains:

---
SEQ ID NO:11:

Trp Lys Phe Asp Gln Gly Asp Thr Thr Arg Leu Val Glu Tyr Asn Asn Lys Ile Thr Ala Ser Tyr Glu Asp Arg Val Thr Phe Leu Pro Thr Gly Ile Thr Phe Lye Ser Val Thr Arg Glu Asp Xaa Gly Gln Tyr Leu Asp Met Asp

--- wherein Xaa at amino acid residue 43 of SEQ ID NO:11 is selected from the group consisting of Cys and a glycosylated residue.

14. A purified platelet membrane glycoprotein designated F11 having an amino acid sequence which contains:

SEQ ID NO:12: Val Thr Phe Leu Pro Thr Gly Ile Thr Phe Lys.

15. A purified platelet membrane glycoprotein designated F11 having an amino acid sequence which contains:

SEQ ID NO:13: Leu Thr Asp Xaa Gly Gln.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( C ) STRANDEDNESS: single (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:1:

```
Xaa Val Thr Val His Ser Ser Glu Pro Glu Val Arg Ile Pro Glu Asn
1               5                   10                  15
Asn Pro Val Lys Leu Xaa Xaa Ala Tyr Xaa Xaa Phe Gln Xaa Pro Xaa
            20              25                  30
Ser Xaa
```

(2) INFORMATION FOR SEQ ID NO:2:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:2:

```
Xaa Xaa Xaa Xaa Xaa Thr Ile Tyr Leu Xaa Xaa Tyr
1               5                   10
```

(2) INFORMATION FOR SEQ ID NO:3:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:3:

```
Lys Phe Lys Leu Ile Val Leu Val
1               5
```

(2) INFORMATION FOR SEQ ID NO:4:

(i) SEQUENCE CHARACTERISTICS:
    (A) LENGTH: 18 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal ( x i ) SEQUENCE DESCRIPTION: SEQ ID NO:4:

| Asp | Xaa | Xaa | Xaa | Xaa | Xaa | Xaa | Xaa | Xaa | Ile | Thr | Phe | Lys | Ser | Val | Thr |
|---|---|---|---|---|---|---|---|---|---|---|---|---|---|---|---|
| 1 | | | | 5 | | | | | 10 | | | | | 15 | |

Arg Xaa ( 2 ) INFORMATION FOR SEQ ID NO:5:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

| Xaa | Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| 1 | | | | 5 | | | | | 10 | | | | | 15 | |
| Xaa | Ile | Xaa | Xaa | Xaa | Xaa | Xaa | Xaa | Xaa | Xaa | Xaa | Xaa | Leu | Xaa | Xaa | Xaa |
| | | | 20 | | | | | 25 | | | | | 30 | | |
| Xaa | Xaa | Xaa | Lys | Ser | Val | Thr | Arg | Glu | Asp | Xaa | Gly | Xaa | Xaa | Leu | Asp |
| | | 35 | | | | | 40 | | | | | 45 | | | |
| Met | Xaa | | | | | | | | | | | | | | |
| | 50 | | | | | | | | | | | | | | |

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

| Xaa | Thr | Phe | Leu | Pro | Thr | Gly | Ile | Thr | Phe | Lys |
|---|---|---|---|---|---|---|---|---|---|---|
| 1 | | | | 5 | | | | | 10 | |

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

```
Leu  Xaa  Asp  Xaa  Xaa  Xaa
1              5
```

( 2 ) INFORMATION FOR SEQ ID NO:8:

( i ) SEQUENCE CHARACTERISTICS:
      ( A ) LENGTH: 34 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:8:

```
Ser  Val  Thr  Val  His  Ser  Ser  Glu  Pro  Glu  Val  Arg  Ile  Pro  Glu  Asn
1              5                        10                           15
Asn  Pro  Val  Lys  Leu  Ser  Cys  Ala  Tyr  Gly  Met  Phe  Gln  Xaa  Pro  Xaa
               20                       25                      30
Ser  Gly
```

( 2 ) INFORMATION FOR SEQ ID NO:9:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:9:

```
Phe  Asp  Lys  Asp  Xaa  Thr  Ile  Tyr  Leu  Asn  Xaa  Tyr
1              5                        10
```

( 2 ) INFORMATION FOR SEQ ID NO:10:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:10:

```
Asp  Arg  Val  Thr  Phe  Leu  Pro  Thr  Gly  Ile  Thr  Phe  Lys  Ser  Val  Thr
1              5                        10                           15
Arg  Glu
```

( 2 ) INFORMATION FOR SEQ ID NO:11:

( i ) SEQUENCE CHARACTERISTICS:

(A) LENGTH: 50 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:11:

```
Trp Lys Phe Asp Gln Gly Asp Thr Thr Arg Leu Val Glu Tyr Asn Asn
1               5                   10                  15

Lys Ile Thr Ala Ser Tyr Glu Asp Arg Val Thr Phe Leu Pro Thr Gly
            20                  25                  30

Ile Thr Phe Lys Ser Val Thr Arg Glu Asp Xaa Gly Gln Tyr Leu Asp
        35                  40                  45

Met Asp
    50
```

(2) INFORMATION FOR SEQ ID NO:12:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:12:

```
Val Thr Phe Leu Pro Thr Gly Ile Thr Phe Lys
1               5                   10
```

(2) INFORMATION FOR SEQ ID NO:13:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:13:

```
Leu Thr Asp Xaa Gly Gln
1               5
```